US012109411B2

(12) United States Patent
Rodriguez et al.

(10) Patent No.: US 12,109,411 B2
(45) Date of Patent: Oct. 8, 2024

(54) SYSTEMS AND METHODS FOR DETECTING FAULT CONDITIONS IN ELECTROPORATION THERAPY

(71) Applicant: OncoSec Medical Incorporated, San Diego, CA (US)

(72) Inventors: John Rodriguez, Vista, CA (US); Jason Jin, Irvine, CA (US); Brandon Dang Phung, San Diego, CA (US); Wesley Joel Ericson, Wyoming, MN (US); Jodie Marie Houdek, Forest Lake, MN (US); Jonathan Joseph McIntosh, Centerville, MN (US); Carlos E. Gonzalez, Firth, ID (US); Anthony Steven Nault, New Brighton, MN (US)

(73) Assignee: GRAND DECADE DEVELOPMENTS LIMITED, Hong Kong (HK)

( * ) Notice: Subject to any disclaimer, the term of this patent is extended or adjusted under 35 U.S.C. 154(b) by 286 days.

(21) Appl. No.: 17/304,605

(22) Filed: Jun. 23, 2021

(65) Prior Publication Data
US 2021/0353938 A1    Nov. 18, 2021

Related U.S. Application Data

(63) Continuation of application No. 16/269,022, filed on Feb. 6, 2019, now Pat. No. 11,071,860.

(51) Int. Cl.
A61N 1/32 (2006.01)
A61B 18/14 (2006.01)
(Continued)

(52) U.S. Cl.
CPC .......... A61N 1/327 (2013.01); A61B 18/1477 (2013.01); A61N 1/0412 (2013.01);
(Continued)

(58) Field of Classification Search
CPC .... A61N 1/327; A61N 1/0412; A61N 1/0476; A61N 1/08; A61N 1/025; A61N 1/0502;
(Continued)

(56) References Cited

U.S. PATENT DOCUMENTS 6,387,671 B1    5/2002  Rubinsky et al.
6,912,417 B1    6/2005  Bernard et al.
(Continued)

FOREIGN PATENT DOCUMENTS

CN    103446667 A    10/1998
CN      1195997 A     3/2005
(Continued)

OTHER PUBLICATIONS

Chenguo et al. "Study on electroporation of cell membrane and tumor treatment," High Voltage Engineering, 30(1):45-47, 51, (Jan. 18, 2004).
(Continued)

Primary Examiner — Rex R Holmes
(74) Attorney, Agent, or Firm — Procopio, Cory, Hargreaves & Savitch LLP

(57) ABSTRACT

Example systems, apparatuses, methods, and computer program products are disclosed for electroporating cells in a tissue using a set of voltage pulses generated by capacitor charge circuitry based on a voltage supply. An example method includes continuously monitoring a set of characteristics of the voltage supply and the set of voltage pulses; generating a first set of monitor signals based on the set of characteristics; detecting a first fault condition based on the first set of monitor signals; and generating a first crowbar trigger activation signal. The example computer method further includes: detecting a second fault condition based on a second set of monitor signals generated based on the first set of monitor signals; and generating a second crowbar
(Continued)

trigger activation signal. Subsequently, the example computer method includes electrically disconnecting the capacitor charge circuitry from electroporation electrode circuitry based on either the first or second crowbar trigger activation signal.

18 Claims, 27 Drawing Sheets

(51) Int. Cl.
  *A61N 1/04* (2006.01)
  *A61B 18/00* (2006.01)
(52) U.S. Cl.
  CPC .............. *A61B 2018/00613* (2013.01); *A61B 2018/00702* (2013.01); *A61B 2018/00767* (2013.01); *A61N 1/0476* (2013.01)
(58) Field of Classification Search
  CPC .............. A61N 1/325; A61B 18/1477; A61B 2018/00613; A61B 2018/00702; A61B 2018/00767; H02H 3/05; H02H 3/025; H02H 3/08; H02H 3/20; H02H 9/041; H02H 3/16; H03K 3/57; C12M 35/02
  See application file for complete search history.

(56) References Cited

U.S. PATENT DOCUMENTS

| | | | |
|---|---|---|---|
| 7,412,284 | B2 | 8/2008 | Hofmann |
| 7,937,143 | B2 | 5/2011 | Demarais et al. |
| 8,209,006 | B2 † | 6/2012 | Smith |
| 8,738,125 | B1 | 5/2014 | Heller et al. |
| 9,020,605 | B2 † | 4/2015 | McCluskey |
| 10,016,232 | B1 | 7/2018 | Bowers et al. |
| 11,071,860 | B2 | 7/2021 | Rodriguez et al. |
| 2002/0183686 | A1 | 12/2002 | Darvish et al. |
| 2002/0193833 | A1* | 12/2002 | Dimmer ................ A61N 1/327 607/3 |
| 2003/0204161 | A1 | 10/2003 | Ferek-Petric |
| 2004/0068299 | A1 | 4/2004 | Laske et al. |
| 2004/0097965 | A1 | 5/2004 | Gardeski et al. |
| 2005/0049542 | A1 | 3/2005 | Sigg et al. |
| 2005/0052630 | A1 | 3/2005 | Smith et al. |
| 2006/0036210 | A1 | 2/2006 | Zhang et al. |
| 2006/0264807 | A1 | 11/2006 | Westersten et al. |
| 2007/0156082 | A1 | 7/2007 | Scherman |
| 2008/0086107 | A1 | 4/2008 | Roschak |
| 2008/0200912 | A1 | 8/2008 | Long |
| 2009/0247933 | A1 | 10/2009 | Maor et al. |
| 2010/0030211 | A1 | 2/2010 | Davalos et al. |
| 2010/0188785 | A1 | 7/2010 | Gascuel |
| 2010/0191174 | A1 | 7/2010 | Lovell et al. |
| 2010/0204638 | A1* | 8/2010 | Hobbs ................ A61B 18/148 606/41 |
| 2010/0261994 | A1 | 10/2010 | Davalos et al. |
| 2010/0268110 | A1 | 10/2010 | Beltran et al. |
| 2011/0238057 | A1 | 9/2011 | Moss et al. |
| 2012/0109122 | A1 | 5/2012 | Arena et al. |
| 2012/0123318 | A1 | 5/2012 | Ek et al. |
| 2012/0136308 | A1 | 5/2012 | Racz |
| 2012/0310230 | A1 | 12/2012 | Willis |
| 2012/0323165 | A1 | 12/2012 | Broderick et al. |
| 2013/0005228 | A1 | 1/2013 | Kazuno et al. |
| 2013/0006228 | A1 | 1/2013 | Johnson et al. |
| 2013/0066296 | A1 | 3/2013 | Broderick et al. |
| 2013/0107399 | A1* | 5/2013 | Cao .................. H02H 3/08 361/15 |
| 2013/0260425 | A1 | 10/2013 | Doi et al. |
| 2013/0260435 | A1 | 10/2013 | Pakhomova et al. |
| 2013/0345779 | A1 | 12/2013 | Maor et al. |
| 2014/0052216 | A1 | 2/2014 | Long et al. |
| 2014/0121728 | A1 | 5/2014 | Dhillon et al. |
| 2014/0148876 | A1 | 5/2014 | Ronchetti et al. |
| 2014/0222105 | A1 | 8/2014 | Broderick et al. |
| 2014/0277219 | A1 | 9/2014 | Nanda |
| 2019/0117964 | A1 | 4/2019 | Bahrami et al. |
| 2020/0246612 | A1 | 8/2020 | Rodriguez et al. |

FOREIGN PATENT DOCUMENTS

| | | | |
|---|---|---|---|
| CN | 103517732 | B | 1/2006 |
| CN | 101370553 | A | 2/2009 |
| CN | 201294372 | Y † | 8/2009 |
| CN | 103781433 | A | 11/2010 |
| CN | 101745178 | B | 12/2011 |
| CN | 101888874 | A | 1/2012 |
| CN | 102625676 | A | 8/2012 |
| CN | 101563132 | A | 1/2013 |
| CN | 102271607 | A | 12/2013 |
| EP | 1515437 | A1 | 3/2014 |
| EP | 2701791 | B1 | 8/2016 |
| JP | 2012-520739 | T | 9/2000 |
| JP | 2004-520865 | T | 9/2012 |
| TW | 200601437 | A | 11/2013 |
| WO | WO 2019/213421 | A1 | 6/1994 |
| WO | WO 00/56395 | A1 | 12/2000 |
| WO | WO 00/77228 | A1 | 4/2002 |
| WO | WO-1994/13804 | A1 | 2/2003 |
| WO | WO-2003/011161 | A1 | 3/2005 |
| WO | WO 02/32335 | A1 | 4/2011 |
| WO | WO 2013/177423 | A2 | 5/2014 |
| WO | WO-2005/021088 | A1 | 9/2016 |
| WO | WO 2011/047387 | A3 | 9/2016 |
| WO | WO 2016/146086 | A2 | 10/2016 |
| WO | WO 2016/161201 | A2 | 11/2019 |

OTHER PUBLICATIONS

Office Action for Chinese Application No. 201680026625.2 dated Jan. 13, 2022.
WIPO Application No. PCT/IB2020/050888, PCT International Preliminary Report on Patentability mailed Aug. 10, 2021.
Brown et al., "Development of an adaptive electroporation system for intratumoral plasmid DNA delivery," Bioelectrochemistry, 122:191-198, (2018).
Ding, Wenjin, "Electroporation Therapy Effect and Development of Research on the Treatment thereof on Tumors (Effect of Electroporation Therapy in Treatment of Tumor: A Research Progress)," Chinese Medical Science, 4(9):48-52, (2014). (English Abstract only).
Dollar et al., "Structured Forests for Fast Edge Detection," IEEE International Conference on Computer Vision, pp. 1841-1848, (Dec. 1, 2013).
Rustamov et al., "Wavelets on Graphs via Deep Learning," Digital Video and Audio Broadcasting Technology: A Practical Engineering Guide (3rd edition), vol. 1, 10 pgs., (Jan. 1, 2013).
Chinese Application No. 201680026625.2, Office Action mailed Apr. 16, 2021.
Chinese Application No. 201680026625.2, Office Action mailed Nov. 18, 2020.
European Application No. 16717025.7, Office Action mailed Jan. 3, 2019.
Extended European Search Report for Application No. 20168699.5, mailed Jul. 6, 2020.
Japanese Application No. 2017-559038, Office Action mailed May 25, 2020.
Taiwanese Application No. 109103711, Office Action mailed Aug. 18, 2020.
U.S. Appl. No. 15/563,462, Final Office Action mailed Mar. 8, 2021.
U.S. Appl. No. 15/563,462, Non-Final Office Action mailed Nov. 19, 2020.
U.S. Appl. No. 16/269,022, Non-Final Office Action mailed Sep. 29, 2020.
WIPO Application No. PCT/IB2020/050888, PCT International Search Report and Written Opinion of the International Searching Authority mailed Apr. 3, 2020.

(56) References Cited

OTHER PUBLICATIONS

WIPO Application No. PCT/US2016/025416, PCT International Search Report and Written Opinion of the International Searching Authority mailed Sep. 23, 2016.
U.S. Appl. No. 16/269,022, filed Feb. 6, 2019, U.S. Pat. No. 11/071,860, Issued.

\* cited by examiner
† cited by third party

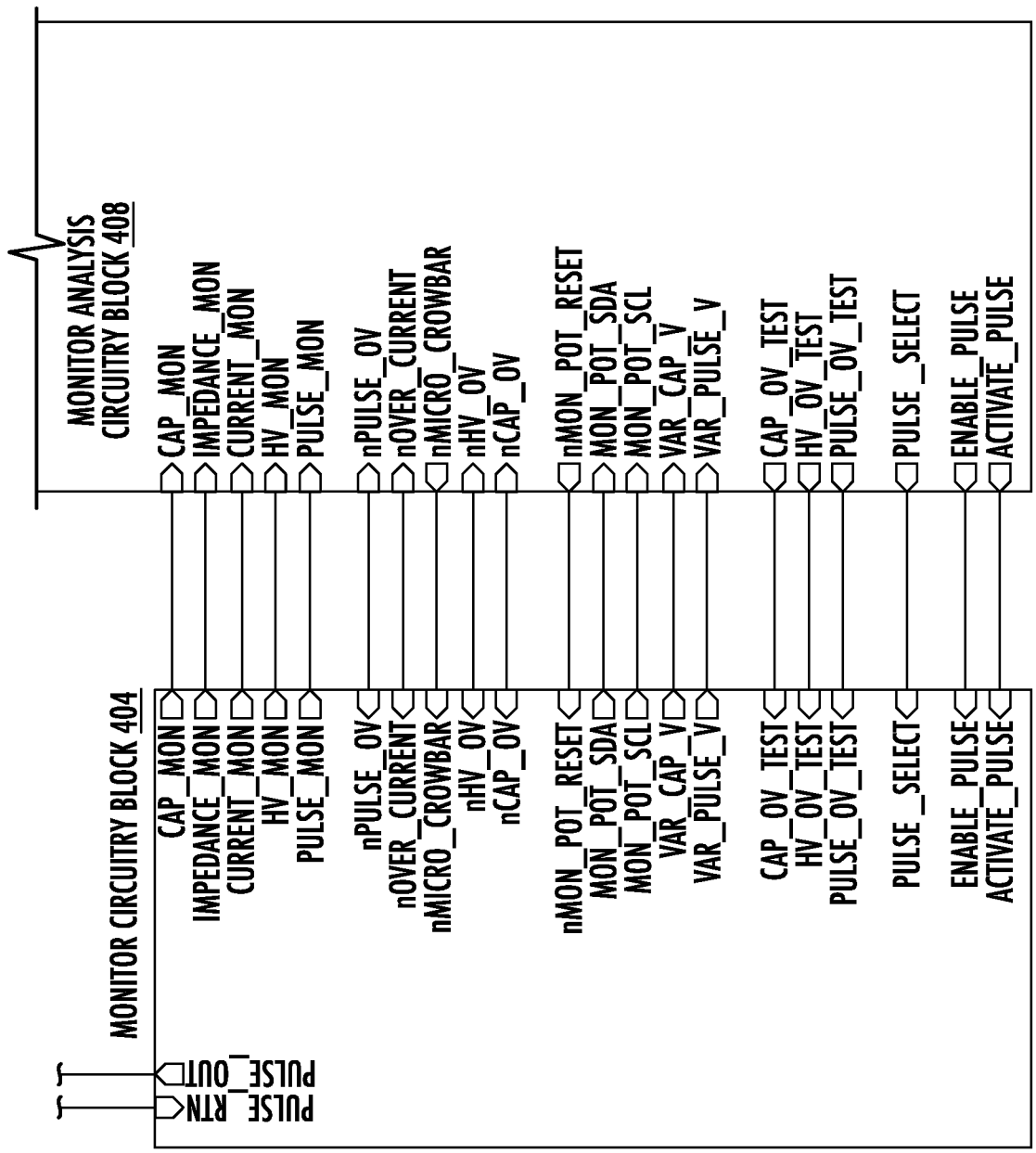
FIG. 4A CONTINUES

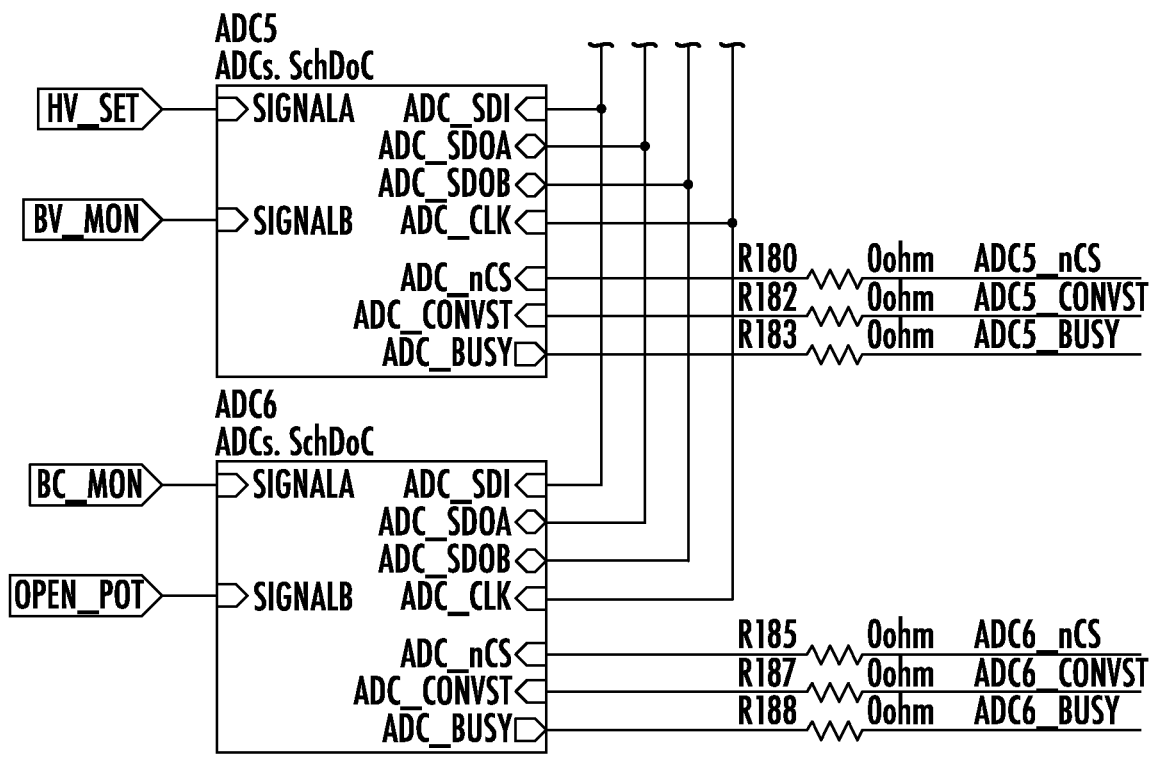
FIG. 4B CONTINUES

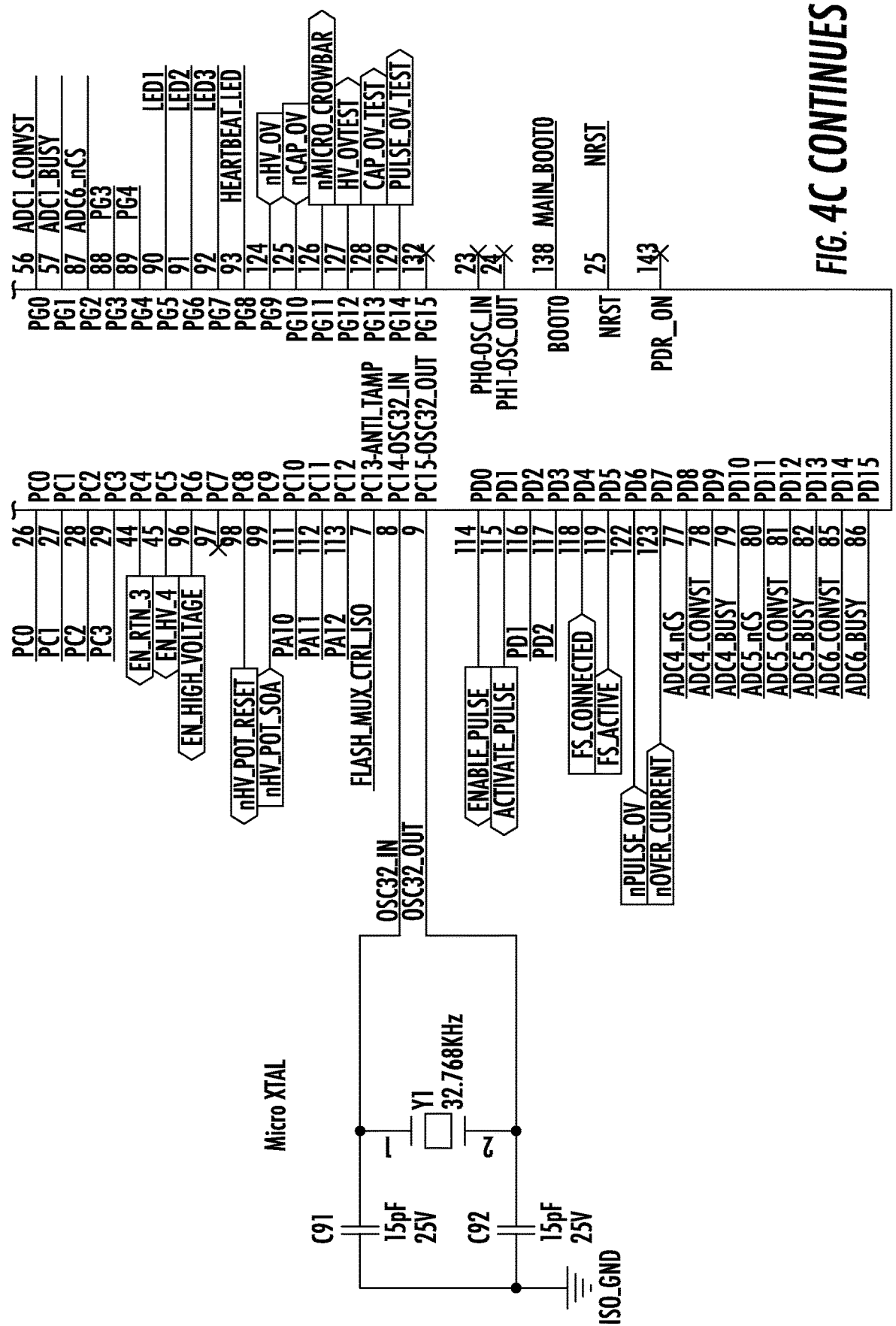
FIG. 4C CONTINUES

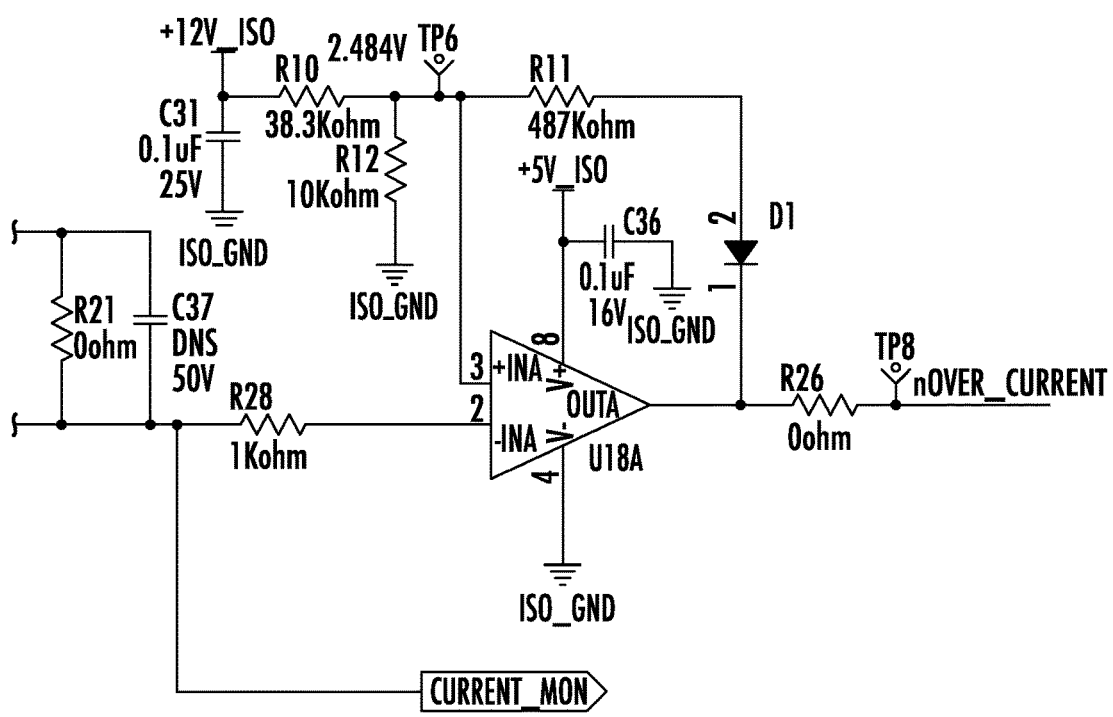
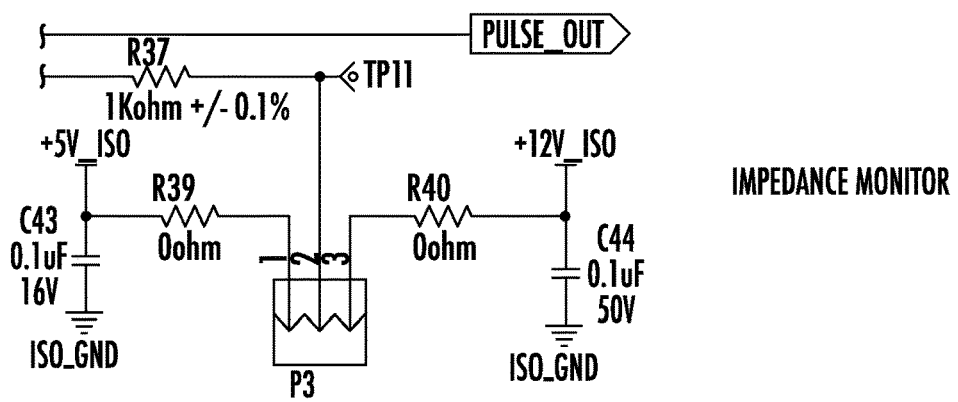
IMPEDANCE MONITOR
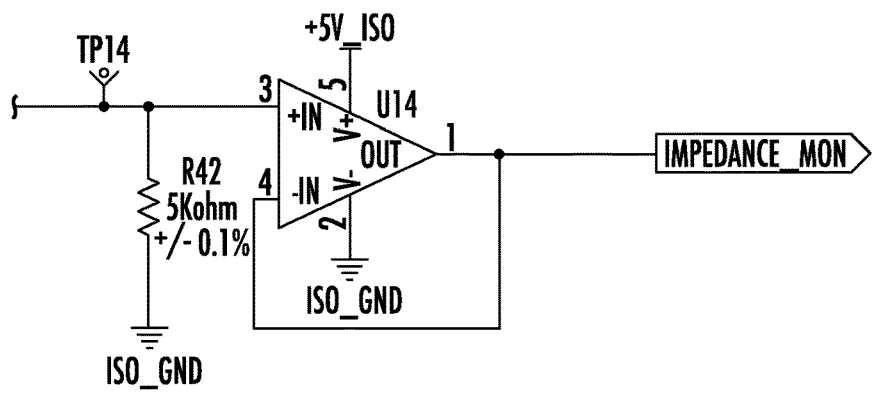
FIG. 5F CONTINUES

SYSTEMS AND METHODS FOR DETECTING FAULT CONDITIONS IN ELECTROPORATION THERAPY

CROSS-REFERENCE TO RELATED APPLICATIONS

This application is a continuation of and claims priority to U.S. patent application Ser. No. 16/269,022, filed Feb. 6, 2019 and now issued as U.S. Pat. No. 11,071,860, which is incorporated herein by reference in its entirety.

TECHNOLOGICAL FIELD

Example embodiments of the present disclosure relate generally to the use of control systems to improve an electroporation process and to increase the permeability of cells, and more specifically to the optimized application of controlled electric fields for delivery of therapeutic moieties into cells by electroporation therapy (EPT), also known as cell poration therapy (CPT) and electrochemotherapy (ECT).

BACKGROUND

In the 1970's scientists discovered that electric fields could be used to create pores in cells without causing permanent damage. This discovery made possible the insertion of large molecules into cell cytoplasm. As a result, therapeutic moieties such as pharmacological compounds now can be incorporated into live cells through a process known as electroporation. The genes or other molecules are injected into the live cells in and short pulses of high electric fields are applied. The cell membranes are transiently made porous and the genes or molecules enter the cells, where they can modify the genome of the cell.

In the treatment of certain types of cancer with chemotherapy, it is necessary to use a high enough dose of a drug to kill the cancer cells without killing an unacceptably high number of normal cells. If the chemotherapy drug could be inserted directly inside the cancer cells, this objective could be achieved. Some of the anti-cancer drugs, for example, bleomycin, normally cannot penetrate the membranes of certain cancer cells effectively. However, electroporation makes it possible to insert bleomycin into cells.

Treatment typically is carried out by injecting an anticancer drug directly into the tumor and applying an electric field to the tumor between a pair of electrodes. The field strength must be adjusted reasonably accurately so that electroporation of the cells of the tumor occurs without damage, or at least minimal damage, to any normal or healthy cells. This can normally be easily carried out with external tumors by applying the electrodes to opposite sides of the tumor so that the electric field is between the electrodes. When the field is uniform, the distance between the electrodes can then be measured and a suitable voltage according to the formula $E=V/d$ can then be applied to the electrodes (E-electric field strength in V/cm; V=voltage in volts; and d=distance in cm). When large or internal tumors are to be treated, it is not easy to properly locate electrodes and measure the distance between them.

Treatment of a subject using cell poration therapy provides a means for avoiding the deleterious effects typically associated with administration of anticancer or cytotoxic agents. Such treatment would allow introduction of these agents to selectively damage or kill undesirable cells while avoiding surrounding healthy cells or tissue. One issue, however, with using electroporation techniques is that diseased tissue, particularly cancerous tissue, can be quite heterogeneous, requiring adjustment of electroporation conditions.

Applicant has identified a number of deficiencies and problems associated with conventional EPT techniques and electroporation systems, and safety features associated therewith. Through applied effort, ingenuity, and innovation, many of these identified problems have been solved by developing solutions that are included in embodiments of the present disclosure, many examples of which are described in detail herein.

SUMMARY

Systems, apparatuses, methods, and computer program products are disclosed herein for electroporating cells in a tissue using a set of continuously monitored voltage pulses generated based on a continuously monitored voltage supply. Although the disclosure herein pertains to any voltage ranges, example embodiments will be described with reference to high voltage (HV) and low voltage (LV) ranges.

In one example embodiment, a system is provided for electroporating cells in a tissue using a set of voltage pulses generated based on a voltage supply. The system may comprise voltage generation circuitry in electrical communication with capacitor charge circuitry and monitor circuitry. The voltage generation circuitry may be configured to generate the voltage supply and transmit the voltage supply to the capacitor charge circuitry. The system may further comprise the capacitor charge circuitry. The capacitor charge circuitry may be in electrical communication with the voltage generation circuitry, crowbar trigger circuitry, the monitor circuitry, and electroporation electrode (EPE) circuitry. The capacitor charge circuitry may be configured to receive the voltage supply from the voltage generation circuitry, generate the set of voltage pulses based on the voltage supply, and transmit the set of voltage pulses to the electroporation electrode circuitry. The system may further comprise the monitor circuitry. The monitor circuitry may be in electrical communication with the voltage generation circuitry, the capacitor charge circuitry, monitor analysis circuitry, and the crowbar trigger circuitry. The monitor circuitry may be configured to continuously monitor a set of characteristics of the voltage supply and the set of voltage pulses, generate a first set of monitor signals based on the set of characteristics, and transmit the first set of monitor signals. The monitor circuitry may be further configured to: detect a first fault condition based on the first set of monitor signals; in response to detection of the first fault condition, generate a first crowbar trigger activation signal; and transmit the first crowbar trigger activation signal to the crowbar trigger circuitry. The system may further comprise the monitor analysis circuitry. The monitor analysis circuitry may be in electrical communication with the crowbar trigger circuitry. The monitor analysis circuitry may be configured to: receive a second set of monitor signals generated based on the first set of monitor signals; detect a second fault condition based on the second set of monitor signals; in response to detection of the second fault condition, generate a second crowbar trigger activation signal; and transmit the second crowbar trigger activation signal to the crowbar trigger circuitry. The system may further comprise the crowbar trigger circuitry. The crowbar trigger circuitry may be in electrical communication with the monitor circuitry and the monitor analysis circuitry. The crowbar trigger circuitry may be configured to: receive the first crowbar trigger activation signal from the monitor circuitry; receive the second crowbar trigger activation signal from the monitor analysis circuitry; and, in response to either receipt of the first crowbar trigger activation signal or receipt of the second crowbar trigger activation signal, electrically disconnect the capacitor charge circuitry from the electroporation electrode circuitry.

In another example embodiment, an apparatus is provided for electroporating cells in a tissue using a set of voltage pulses generated based on a voltage supply. The apparatus may comprise voltage generation circuitry in electrical communication with capacitor charge circuitry and monitor circuitry. The voltage generation circuitry may be configured to generate the voltage supply and transmit the voltage supply to the capacitor charge circuitry. The apparatus may further comprise the capacitor charge circuitry. The capacitor charge circuitry may be in electrical communication with the voltage generation circuitry, crowbar trigger circuitry, the monitor circuitry, and electroporation electrode circuitry. The capacitor charge circuitry may be configured to receive the voltage supply from the voltage generation circuitry, generate the set of voltage pulses based on the voltage supply, and transmit the set of voltage pulses to the electroporation electrode circuitry. The apparatus may further comprise the monitor circuitry. The monitor circuitry may be in electrical communication with the voltage generation circuitry, the capacitor charge circuitry, monitor analysis circuitry, and the crowbar trigger circuitry. The monitor circuitry may be configured to continuously monitor a set of characteristics of the voltage supply and the set of voltage pulses, generate a first set of monitor signals based on the set of characteristics, and transmit the first set of monitor signals. The monitor circuitry may be further configured to: detect a first fault condition based on the first set of monitor signals; in response to detection of the first fault condition, generate a first crowbar trigger activation signal; and transmit the first crowbar trigger activation signal to the crowbar trigger circuitry. The apparatus may further comprise the monitor analysis circuitry. The monitor analysis circuitry may be in electrical communication with the crowbar trigger circuitry. The monitor analysis circuitry may be configured to: receive a second set of monitor signals generated based on the first set of monitor signals; detect a second fault condition based on the second set of monitor signals; in response to detection of the second fault condition, generate a second crowbar trigger activation signal; and transmit the second crowbar trigger activation signal to the crowbar trigger circuitry. The apparatus may further comprise the crowbar trigger circuitry. The crowbar trigger circuitry may be in electrical communication with the monitor circuitry and the monitor analysis circuitry. The crowbar trigger circuitry may be configured to: receive the first crowbar trigger activation signal from the monitor circuitry; receive the second crowbar trigger activation signal from the monitor analysis circuitry; and, in response to either receipt of the first crowbar trigger activation signal or receipt of the second crowbar trigger activation signal, electrically disconnect the capacitor charge circuitry from the electroporation electrode circuitry.

In another example embodiment, an apparatus is provided for electroporating cells in a tissue using a set of voltage pulses generated based on a voltage supply. The apparatus may comprise monitor circuitry in electrical communication with crowbar trigger circuitry. The monitor circuitry may be configured to continuously monitor a set of characteristics of the voltage supply and the set of voltage pulses. The monitor circuitry may be further configured to generate a first set of monitor signals based on the set of characteristics. The monitor circuitry may be further configured to transmit the first set of monitor signals. The monitor circuitry may be further configured to detect a first fault condition based on the first set of monitor signals. The monitor circuitry may be further configured to, in response to detection of the first fault condition, generate a first crowbar trigger activation signal. The monitor circuitry may be further configured to transmit the first crowbar trigger activation signal to the crowbar trigger circuitry. The apparatus may further comprise monitor analysis circuitry in electrical communication with the crowbar trigger circuitry. The monitor analysis circuitry may be configured to receive a second set of monitor signals generated based on the first set of monitor signals. The monitor analysis circuitry may be further configured to detect a second fault condition based on the second set of monitor signals. The monitor analysis circuitry may be further configured to, in response to detection of the second fault condition, generate a second crowbar trigger activation signal. The monitor analysis circuitry may be further configured to transmit the second crowbar trigger activation signal to the crowbar trigger circuitry. The apparatus may further comprise the crowbar trigger circuitry. The crowbar trigger circuitry may be in electrical communication with the monitor circuitry and the monitor analysis circuitry. The crowbar trigger circuitry may be configured to receive the first crowbar trigger activation signal from the monitor circuitry. The crowbar trigger circuitry may be further configured to receive the second crowbar trigger activation signal from the monitor analysis circuitry. The crowbar trigger circuitry may be further configured to, in response to either receipt of the first crowbar trigger activation signal or receipt of the second crowbar trigger activation signal, electrically disconnect the voltage supply from electroporation electrode circuitry.

In another example embodiment, a method is provided for electroporating cells in a tissue using a set of voltage pulses generated based on a voltage supply. The method may comprise: generating, by voltage generation circuitry, the voltage supply; and transmitting, by the voltage generation circuitry, the voltage supply to capacitor charge circuitry. The method may further comprise: receiving, by the capacitor charge circuitry, the voltage supply from the voltage generation circuitry; generating, by the capacitor charge circuitry, the set of voltage pulses based on the voltage supply; and transmitting, by the capacitor charge circuitry, the set of voltage pulses to electroporation electrode circuitry. The method may further comprise: continuously monitoring, by monitor circuitry, a set of characteristics of the voltage supply and the set of voltage pulses; generating, by the monitor circuitry, a first set of monitor signals based on the set of characteristics; transmitting, by the monitor circuitry, the first set of monitor signals; detecting, by the monitor circuitry, a first fault condition based on the first set of monitor signals; in response to detecting the first fault condition, generating, by the monitor circuitry, a first crowbar trigger activation signal; and transmitting, by the monitor circuitry, the first crowbar trigger activation signal to crowbar trigger circuitry. The method may further comprise: receiving, by monitor analysis circuitry, a second set of monitor signals generated based on the first set of monitor signals; detecting, by the monitor analysis circuitry, a second fault condition based on the second set of monitor signals; in response to detecting the second fault condition, generating, by the monitor analysis circuitry, a second crowbar trigger activation signal; and transmitting, by the monitor analysis circuitry, the second crowbar trigger activation signal to the crowbar trigger circuitry. The method may further comprise: receiving, by the crowbar trigger circuitry, either the first crowbar trigger activation signal or the second crowbar trigger activation signal; and in response to either receiving the first crowbar trigger activation signal or receiving the second crowbar trigger activation signal, electrically disconnecting, by the crowbar trigger circuitry, the capacitor charge circuitry from the electroporation electrode circuitry.

In yet another example embodiment, a computer program product is provided for electroporating cells in a tissue using a set of voltage pulses generated based on a voltage supply. The computer program product may comprise at least one non-transitory computer-readable storage medium storing computer-executable program code instructions that, when executed by a computing system, cause the computing system to: generate, by voltage generation circuitry, the voltage supply; and transmit, by the voltage generation circuitry, the voltage supply to capacitor charge circuitry. The computer-executable program code instructions, when executed by the computing system, may further cause the computing system to: receive, by the capacitor charge circuitry, the voltage supply from the voltage generation circuitry; generate, by the capacitor charge circuitry, the set of voltage pulses based on the voltage supply; and transmit, by the capacitor charge circuitry, the set of voltage pulses to electroporation electrode circuitry. The computer-executable program code instructions, when executed by the computing system, may further cause the computing system to receive, by monitor analysis circuitry, a second set of monitor signals generated based on a first set of monitor signals. The first set of monitor signals may have been generated, by monitor circuitry, based on a continuously monitored set of characteristics of the voltage supply and the set of voltage pulses. The computer-executable program code instructions, when executed by the computing system, may further cause the computing system to: detect, by the monitor analysis circuitry, a fault condition based on the second set of monitor signals; in response to detecting the fault condition, generate, by the monitor analysis circuitry, a crowbar trigger activation signal; and transmit, by the monitor analysis circuitry, the crowbar trigger activation signal to the crowbar trigger circuitry. The computer-executable program code instructions, when executed by the computing system, may further cause the computing system to: receive, by the crowbar trigger circuitry, either the first crowbar trigger activation signal or the second crowbar trigger activation signal; and in response to either receiving the first crowbar trigger activation signal or receiving the second crowbar trigger activation signal, electrically disconnecting, by the crowbar trigger circuitry, the capacitor charge circuitry from the electroporation electrode circuitry.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings, which illustrate example embodiments and features of the present disclosure and are not necessarily drawn to scale. It will be understood that the components and structures illustrated in the drawings may or may not be present in various embodiments of the disclosure described herein. Accordingly, some embodiments or features of the present disclosure may include fewer or more components or structures than those shown in the drawings while not departing from the scope of the disclosure.

FIG. 5A, FIG. 5B, FIG. 5C, FIG. 5D, FIG. 5E, FIG. 5F, FIG. 5G, FIG. 5H, FIG. 5I, and FIG. 5J illustrate example schematic diagrams in accordance with some example embodiments described herein.

DETAILED DESCRIPTION

Figure 1:
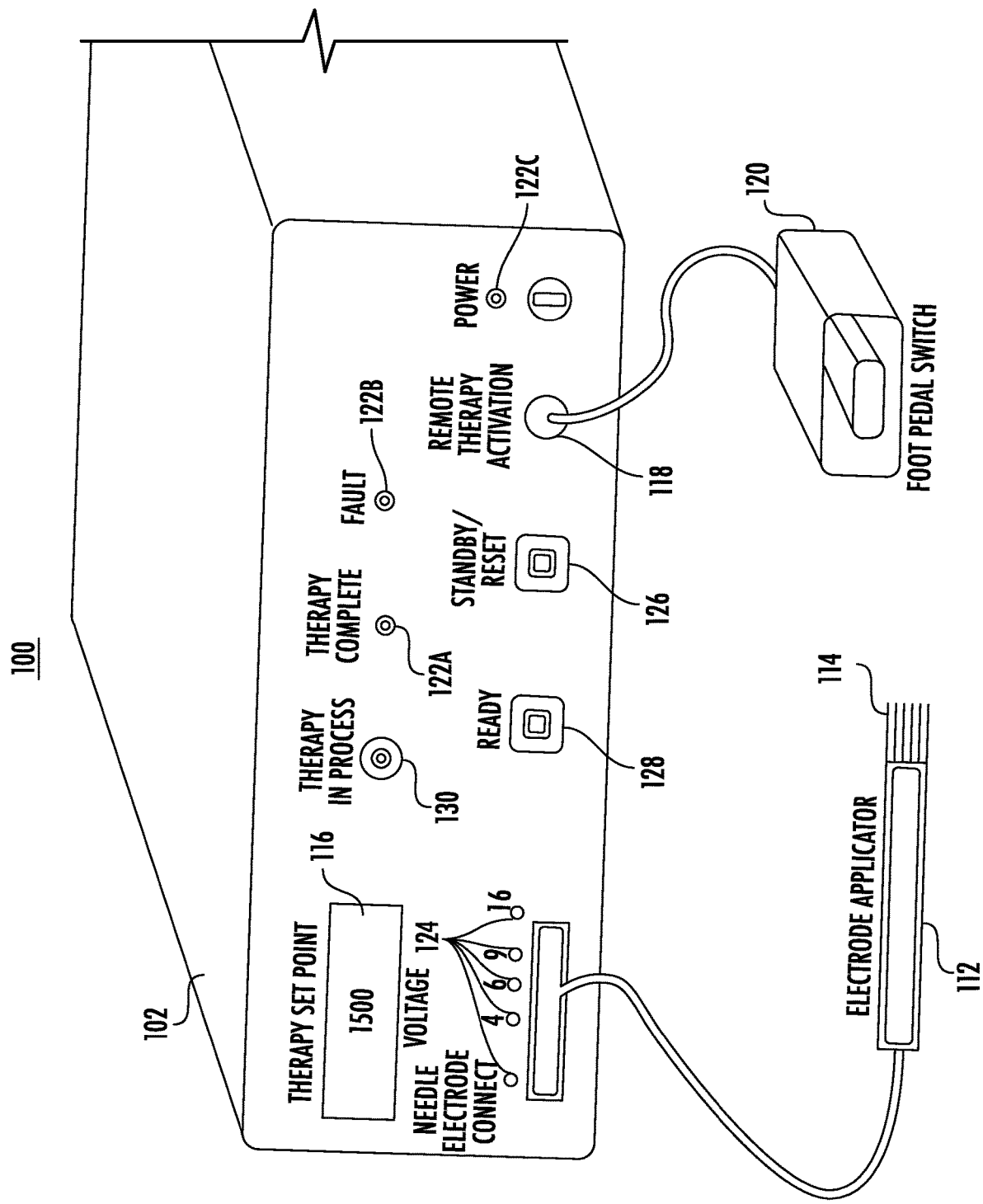
FIG. 1 illustrates an example EPT treatment instrument in accordance with some example embodiments described herein.

The following description should be read with reference to the drawings wherein like reference numerals indicate like elements throughout the several views. The detailed description and drawings show several embodiments which are meant to be illustrative of the disclosure. It should be understood that any numbering of disclosed features (e.g., first, second, etc.) and/or directional terms used in conjunction with disclosed features (e.g., front, back, under, above, etc.) are relative terms indicating illustrative relationships between the pertinent features.

It should be understood at the outset that although illustrative implementations of one or more aspects are illustrated below, the disclosed assemblies, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

The word "example," when used herein, is intended to mean "serving as an example, instance, or illustration." Any implementation described herein as an "example" is not necessarily preferred or advantageous over other implementations.

Example embodiments described herein provide systems, apparatuses, methods, and computer program products for an EPT treatment instrument which provides for electroporating cells in a tissue using a set of pulses (e.g., HV pulses, LV pulses) generated based on a voltage supply (e.g., an HV supply, an LV supply). In some instances, the EPT treatment instrument may provide redundant safety protocols comprising hardware-based safety protocols (e.g., monitor circuitry 240) and software-based safety protocols (e.g., executed by monitor analysis circuitry 270). For example, the EPT treatment instrument disclosed herein provides for detecting fault conditions using four hardware monitoring circuitries in addition to four software monitoring circuitries, each of which is configured to activate the crowbar trigger circuitry described herein in the event of a fault condition (e.g., overvoltage, overcurrent). Further, if the crowbar trigger circuitry fails, the relay circuitry described herein comprises two relays configured to cut off power and prevent dissipation of the overvoltage or overcurrent to the patient.

In some embodiments, the EPT treatment instrument disclosed herein provides for: continuously monitoring a set of characteristics of the voltage supply and the set of voltage pulses; generating a set of analog monitor signals based on the set of characteristics; detecting a first fault condition (e.g., overvoltage, overcurrent) based on the analog set of monitor signals; detecting a second fault condition based on a set of digital monitor signals; and in response to either the detection of the first fault condition or the second fault condition, electrically disconnecting, by crowbar trigger circuitry, the voltage pulses and the voltage supply from the electroporation electrode needles to prevent the overvoltages and overcurrents from being applied to the patient.

In some embodiments, the EPT treatment instrument disclosed herein provides for using a lower voltage (e.g., 5 volts instead of 50 volts) during needle placement verification to provide improved safety for the patient while verifying that the EPE needle electrode is properly in place. For example, the EPT treatment instrument may be used with a low voltage electroporation assembly to provide for the detection of proper tissue resistance and applicator resistance. In some embodiments, the voltage used for low voltage applications is about 5 Vdc, In some embodiments, the voltages used for high voltage applications are between about 400 Vdc and about 1300 Vdc.

There are many advantages of the embodiments disclosed herein, such as: improved detection of a fault condition by multiple, redundant analog and digital circuitries; preventing, by crowbar trigger circuitry, any overvoltages or overcurrents from being applied to a patient; improved patient safety by using lower voltage pulses during needle placement verification; and increasing the speed of charging the capacitor charge circuitry because the impedance monitor circuitry, rather than the capacitor charge circuitry, is used for needle placement verification.

FIG. 1 is a diagram of an EPT treatment instrument 100 for electroporating cells in a tissue using a set of pulses (e.g., HV pulses, LV pulses) generated based on a voltage supply. An electroporation electrode applicator 112 may be removably coupled to the EPT treatment instrument 100, which may be configured to selectively apply voltage pulses to selected electroporation electrode needles 114 of the electroporation electrode applicator 112. The pulse duration, voltage level, and electroporation electrode needle addressing or switching pattern output by the EPT treatment instrument 100 are all programmable.

A display 116 indicates the therapy voltage setpoint. A remote therapy activation connection 118 is provided to accommodate a foot pedal switch 120 for activating pulses to the electroporation electrode applicator 112. The foot pedal switch 120 permits a physician to activate the EPT treatment instrument 100 while freeing both hands for positioning of the electroporation electrode applicator 112 in a patient's tissue. Status indicator lights 122 for power on (122A), fault detection (122B), and completion of a therapy session (122C) are provided for convenience. Electroporation electrode indicator lights 124 are provided to positively indicate that an electroporation electrode applicator 112 is connected to the EPT treatment instrument 100 and to indicate the type of electroporation electrode needle array (e.g., 4, 6, 9, or 16 electroporation electrode needles). A standby/reset button 126 is provided to "pause" the instrument and reset all functions of the EPT treatment instrument 100 to a default state. A ready button 128 is provided to prepare the EPT treatment instrument 100 for a therapy session. A prominent "therapy in process" indicator light 130 indicates that voltage pulses are being applied to the electroporation electrode needles 114. In addition, the EPT treatment instrument 100 may have audio indicators for such functions as a button press, a fault state, commencement or termination of a therapy session, indication of therapy in process, and other suitable functions.

In some embodiments, the EPT treatment instrument 100 may provide for electroporating cells in a tissue using a set of voltage pulses generated based on a voltage supply. The EPT treatment instrument 100 may provide for generating the voltage supply, generating the set of voltage pulses based on the voltage supply, and transmitting the set of voltage pulses to the electroporation electrode needles 114. The EPT treatment instrument 100 may further provide for: continuously monitoring a set of characteristics of the voltage supply and the set of voltage pulses; generating a set of analog monitor signals based on the set of characteristics; detecting a first fault condition (e.g., overvoltage, overcurrent) based on the analog set of monitor signals; detecting a second fault condition (e.g., overvoltage, overcurrent) based on a set of digital monitor signals (e.g., digitized versions of the analog set of monitor signals); and in response to either the detection of the first fault condition or the second fault condition, electrically disconnecting, by crowbar trigger circuitry disposed in the EPT treatment instrument 100, the voltage pulses and the voltage supply from the electroporation electrode needles 114 to prevent the overvoltages and overcurrents from being applied to the patient.

In some embodiments, the EPT treatment instrument 100 may be coupled to a feedback sensor configured to detect the patient's heart beats. By synchronizing the application of voltage pulses near the heart to safe periods between heart beats, the possibility of the applied voltage pulses interfering with normal heart rhythms may be reduced. Additional disclosure relating to EPT treatment instruments and the advantages thereof are disclosed in U.S. Pat. No. 7,412,284, issued Aug. 12, 2008, and U.S. patent application Ser. No. 15/563,462, filed Sep. 29, 2017, both of which are herein incorporated by reference in their entireties.

The EPT treatment instrument 100 described with reference to FIG. 1 may be embodied by one or more apparatuses, such as apparatus 200 shown in FIG. 2. The apparatus 200 may be configured to execute the operations described above with respect to FIG. 1 and below with respect to FIG. 3A, FIG. 3B, FIG. 3C, FIG. 3D, FIG. 4A, FIG. 4B, FIG. 4C, FIG. 5A, FIG. 5B, FIG. 5C, FIG. 5D, FIG. 5E, FIG. 5F, FIG. 5G, FIG. 5H, FIG. 5I, FIG. 5J, FIG. 6A, FIG. 6B, FIG. 6C and FIG. 7. Although some of these components 210-296 are described with respect to their functional capabilities, it should be understood that the particular implementations necessarily include the use of particular hardware to implement such functional capabilities. It should also be understood that certain of these components 210-296 may include similar or common hardware. For example, two sets of circuitry may both leverage use of the same electrical connection, ADC, network interface, processor, memory, or the like to perform their associated functions, such that duplicate hardware is not required for each set of circuitry.

The use of the term "circuitry" as used herein with respect to components of the apparatus 200 therefore includes particular hardware configured to perform the functions associated with respective circuitry described herein. Of course, while the term "circuitry" should be understood broadly to include hardware, in some embodiments, circuitry may also include program code instructions for configuring the hardware. For example, in some embodiments, "circuitry" may include processing circuitry (e.g., digital signal processing (DSP) components), storage media, network interfaces, input-output devices, and other components. In some embodiments, other elements of the apparatus 200 may provide or supplement the functionality of particular circuitry. For example, the processor 262 may provide processing functionality, memory 264 may provide storage functionality, and communications circuitry 268 may provide network interface functionality, among other features.

Figure 2:
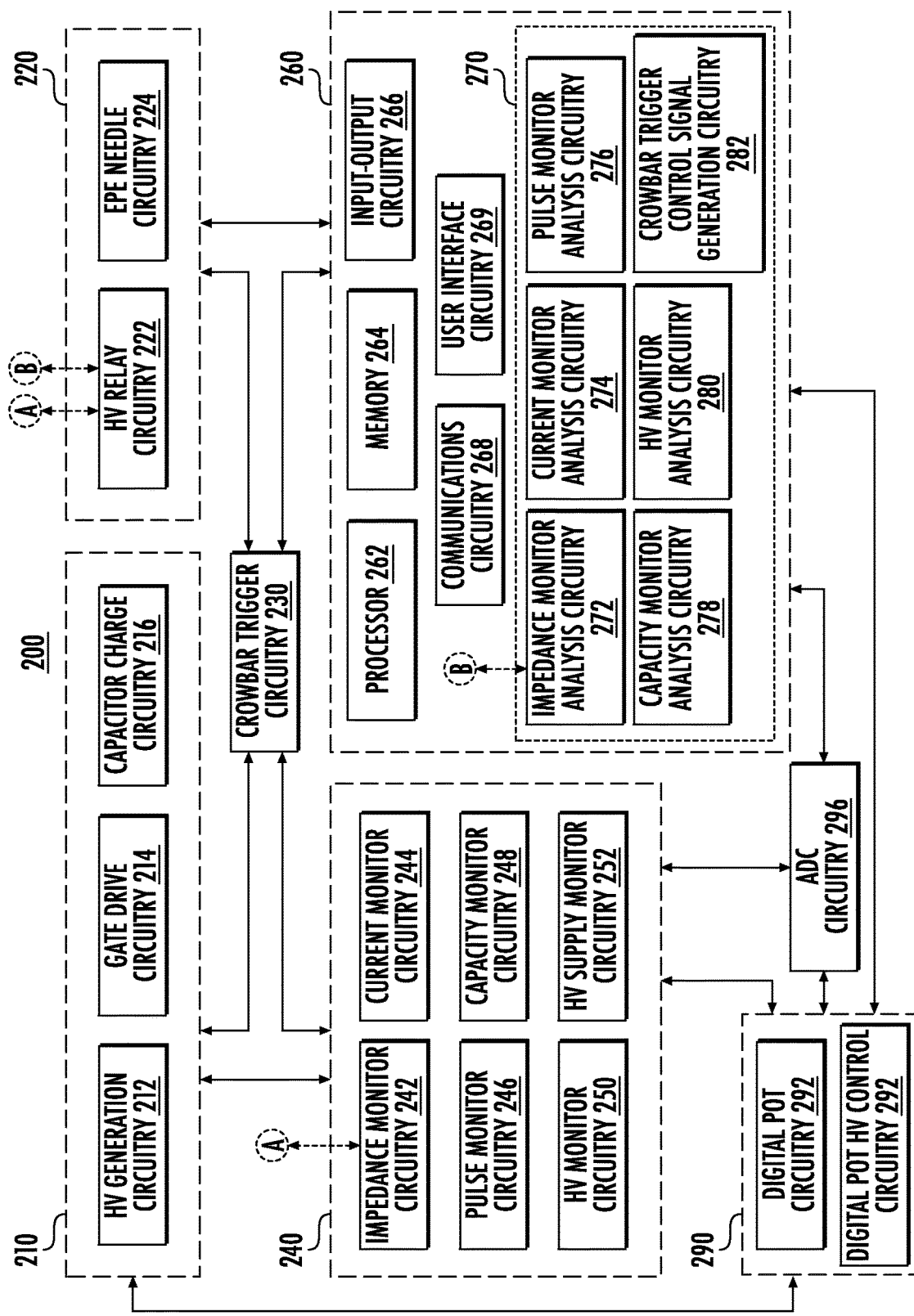
FIG. 2 illustrates an example schematic block diagram in accordance with some example embodiments described herein.

As illustrated in FIG. 2, the apparatus 200 may include HV circuitry 210, electroporation electrode (EPE) circuitry 220, crowbar trigger circuitry 230, monitor circuitry 240 (e.g., hardware-based monitor circuitry), processing circuitry 260, control circuitry 290, and analog-to-digital conversion (ADC) circuitry 296. The HV circuitry 210 may include HV generation circuitry 212, gate drive circuitry 214, and capacitor charge circuitry 216. The EPE circuitry 220 may include HV relay circuitry 222 (e.g., comprising a set of relays) and EPE needle circuitry 224. The monitor circuitry 240 may include impedance monitor circuitry 242, current monitor circuitry 244, pulse monitor circuitry 246, capacity monitor circuitry 248, HV monitor circuitry 250, and HV supply monitor circuitry 252. The processing circuitry 260 may include processor 262, memory 264, input-output circuitry 266, communications circuitry 268, user interface circuitry 269, and monitor analysis circuitry 270 (e.g., software-based monitor circuitry). The monitor analysis circuitry 270 may include impedance monitor analysis circuitry 272, current monitor analysis circuitry 274, pulse monitor analysis circuitry 276, capacity monitor analysis circuitry 278, HV monitor analysis circuitry 280, and crowbar trigger control signal generation circuitry 282. The control circuitry 290 may include digital potentiometer (pot) circuitry 292 and digital pot HV control circuitry 294.

The HV generation circuitry 212 may be in electrical communication with the gate drive circuitry 214, the capacitor charge circuitry 216, the monitor circuitry 240, the processing circuitry 260, the digital pot HV control circuitry 294, and the ADC circuitry 296. The HV generation circuitry 212 may be configured to generate a voltage supply (e.g., an HV supply, an LV supply) and transmit the voltage supply to the capacitor charge circuitry 216. The capacitor charge circuitry 216 may be in electrical communication with the HV generation circuitry 212, the crowbar trigger circuitry 230, the monitor circuitry 240, and the EPE circuitry 220. The capacitor charge circuitry 216 may be configured to receive the voltage supply from the HV generation circuitry 212, generate the set of voltage pulses (e.g., HV pulses, LV pulses) based on the voltage supply, and transmit the set of voltage pulses to the electroporation electrode circuitry 220 (e.g., via HV relay circuitry 222). In some embodiments, a set of voltage pulses may include from about 6 to about 10 pulses per set. In some embodiments, the duration (e.g., pulse width) of each voltage pulse in the set of voltage pulses may be between about 70 microseconds and about 150 microseconds. In some embodiments, the duration (e.g., pulse width) of each voltage pulse in the set of voltage pulses may be from about 100 microseconds to about 1 millisecond. For example, the duration of each voltage pulse in the set of voltage pulses may be about 100 microseconds. In some embodiments, the term "voltage" refers to direct current (DC) voltage, and the term "volts" refers to Vdc. In some embodiments, the HV generation circuitry 212 may be referred to as "voltage generation circuitry" and may comprise HV generation circuitry configured to generate an HV supply, LV generation circuitry configured to generate an LV supply, or both. In other embodiments, the LV generation circuitry may be comprised by the apparatus 200 apart from the HV generation circuitry. In some embodiments, the voltage of the HV supply may be between about 600 volts and 3,000 volts, using a field strength of 700V/cm or greater. In some embodiments, the voltage of the HV supply may be between about 1,000 volts and 1,750 volts, and the amperage of the HV supply may be between about 40 amps and 60 amps. For example, the voltage of the HV supply may be about 1,500 volts, and the amperage of the HV supply may be about 70 amps. In some embodiments, the voltage of the HV supply may be between about 400 volts and 1,300 volts. In some embodiments, the voltage of an LV supply generated by the HV generation circuitry 212 or by a separate LV generation circuitry comprised by the apparatus 200, may be about 5 volts.

The monitor circuitry 240 may be in electrical communication with the HV generation circuitry 212, the capacitor charge circuitry 216, monitor analysis circuitry 270, and the crowbar trigger circuitry 230. The monitor circuitry 240 may be configured to continuously monitor a set of characteristics of the voltage supply and the set of voltage pulses, generate a first set of monitor signals based on the set of characteristics, and transmit the first set of monitor signals to digital pot circuitry 292, ADC circuitry 296. The first set of monitor signals may include a set of analog monitor signals, such as an analog continuously monitored HV voltage signal (HV_MON), an analog continuously monitored capacitor voltage signal (CAP_MON, VAR_CAP_V), an analog continuously monitored pulse voltage signal (PULSE_MON, VAR_PULSE_V), an analog continuously monitored current signal (CURRENT_MON), an analog continuously monitored impedance voltage signal (IMPEDANCE_MON), an analog continuously monitored HV supply voltage signal (BV_MON), an analog continuously monitored HV supply current signal (BC_MON), any other suitable analog monitor signal, or any combination thereof.

The monitor circuitry 240 may be further configured to: detect a first fault condition based on the first set of monitor signals; in response to detection of the first fault condition, generate a first crowbar trigger activation signal; and transmit the first crowbar trigger activation signal to the crowbar trigger circuitry 230. The first fault condition may comprise an analog fault condition, such as an analog HV overvoltage condition, an analog capacitor overvoltage condition, an analog pulse overvoltage signal condition, an analog overcurrent signal condition, any other suitable analog fault condition, or any combination thereof. The first crowbar trigger activation signal may comprise an analog crowbar trigger activation signal, such as an HV overvoltage signal (nHV_OV), a capacitor overvoltage signal (nCAP_OV), a pulse overvoltage signal (nPULSE_OV), an overcurrent signal (nOVER_CURRENT), any other suitable analog crowbar trigger activation signal, or any combination thereof.

In some embodiments, the monitor circuitry 240 may comprise HV monitor circuitry 250. The HV monitor circuitry 250 may be configured to: continuously monitor an HV voltage (+HV) of the HV supply, wherein the set of characteristics comprises the continuously monitored HV voltage; generate a first continuously monitored HV voltage signal (HV_MON) based on the continuously monitored HV voltage, wherein the first set of monitor signals comprises the first continuously monitored HV voltage signal; detect a first HV overvoltage condition (e.g., an analog HV voltage above or equal to 1,512 volts for an HV supply voltage of 1,500 volts) based on the first continuously monitored HV voltage signal, wherein the first fault condition is the first HV overvoltage condition; and, in response to detection of the first HV overvoltage condition, generate a first HV overvoltage signal (nHV_OV), wherein the first crowbar trigger activation signal is the first HV overvoltage signal.

In some embodiments, the monitor circuitry 240 may comprise capacity monitor circuitry 248. The capacity monitor circuitry 248 may be configured to: continuously monitor a capacitor voltage (CAP_V) of the capacitor charge circuitry 216, wherein the set of characteristics comprises the continuously monitored capacitor voltage; generate a first continuously monitored capacitor voltage signal (CAP_MON) based on the continuously monitored capacitor voltage, wherein the first set of monitor signals comprises the first continuously monitored capacitor voltage signal; detect a first capacitor overvoltage condition (e.g., an analog capacitor voltage in excess of an analog capacitor voltage overvoltage (VAR_CAP_V)) based on the first continuously monitored capacitor voltage signal, wherein the first fault condition is the first capacitor overvoltage condition; and, in response to detection of the first capacitor overvoltage condition, generate a first capacitor overvoltage signal (nCAP_OV), wherein the first crowbar trigger activation signal is the first capacitor overvoltage signal.

In some embodiments, the monitor circuitry 240 may comprise pulse monitor circuitry 246. The pulse monitor circuitry 246 may be configured to: continuously monitor a pulse voltage (−HV_PULSE) of the set of HV pulses, wherein the set of characteristics comprises the continuously monitored pulse voltage; generate a first continuously monitored pulse voltage signal (PULSE_MON) based on the continuously monitored pulse voltage, wherein the first set of monitor signals comprises the first continuously monitored pulse voltage signal; detect a first pulse overvoltage condition (e.g., an analog pulse voltage in excess of an analog pulse voltage overvoltage (VAR_PULSE_V)) based on the first continuously monitored pulse voltage signal, wherein the first fault condition is the first pulse overvoltage condition; and in response to detection of the first pulse overvoltage condition, generate a first pulse overvoltage signal (nPULSE_OV), wherein the first crowbar trigger activation signal is the first pulse overvoltage signal.

In some embodiments, the monitor circuitry 240 may comprise current monitor circuitry 244. The current monitor circuitry 244 may be configured to: continuously monitor a current of the set of HV pulses, wherein the set of characteristics comprises the continuously monitored current; generate a first continuously monitored current signal (CURRENT_MON) based on the continuously monitored current, wherein the first set of monitor signals comprises the first continuously monitored current signal; detect a first overcurrent condition (e.g., an analog current in excess of an analog current overcurrent value) based on the first continuously monitored current signal, wherein the first fault condition is the first overcurrent condition; and in response to detection of the first overcurrent condition, generate a first overcurrent signal (nOVER_CURRENT), wherein the first crowbar trigger activation signal is the first overcurrent signal.

In some embodiments, the monitor circuitry 240 may be in electrical communication with a set of relays comprised by the HV relay circuitry 222. The monitor circuitry 240 may comprise impedance monitor circuitry 242. The impedance monitor circuitry 242 may be configured to: generate a set of low voltage (LV) pulses (e.g., 5 volts instead of 50 volts); transmit the set of LV pulses to the electroporation electrode circuitry 220; receive a set of LV return pulses from the electroporation electrode circuitry 220; monitor a resistance of the tissue based on the set of LV return pulses; and generate a first monitored impedance voltage signal (IMPEDANCE_MON) based on the monitored resistance. The impedance monitor circuitry 242 may be further configured to: detect a first impedance testing fault condition (e.g., an analog resistance less than a typical skin resistance (e.g., 20 ohms)) based on the first monitored impedance voltage signal; and, in response to detection of the first impedance testing fault condition, generate a first set of relay deactivation signals; and transmit the first set of relay deactivation signals to the set of relays. Each relay in the set of relays may be configured to: receive one of the relay deactivation signals in the first set of relay deactivation signals from the impedance monitor circuitry 242; and, in response to receipt of the one of the relay deactivation signals in the first set of relay deactivation signals, electrically disconnect the capacitor charge circuitry 216 from the EPE needle circuitry 224.

The monitor analysis circuitry 270 may be in electrical communication with the crowbar trigger circuitry 230 and the ADC circuitry 296. The monitor analysis circuitry 270 may be configured to: receive a second set of monitor signals generated based on the first set of monitor signals; detect a second fault condition based on the second set of monitor signals; in response to detection of the second fault condition, generate a second crowbar trigger activation signal; and transmit the second crowbar trigger activation signal to the crowbar trigger circuitry. The second set of monitor signals may include a set of digital monitor signals, such as a digital continuously monitored HV voltage signal (digital HV_MON), a digital continuously monitored capacitor voltage signal (digital CAP_MON, digital VAR_CAP_V), a digital continuously monitored pulse voltage signal (digital PULSE_MON, digital VAR_PULSE_V), a digital continuously monitored current signal (digital CURRENT_MON), a digital continuously monitored impedance voltage signal (digital IMPEDANCE_MON), a digital continuously monitored HV supply voltage signal (digital BV_MON), a digital continuously monitored HV supply current signal (digital BC_MON), any other suitable digital monitor signal, or any combination thereof. In some embodiments, the monitor analysis circuitry 270 may be configured to receive the second set of monitor signals from the ADC circuitry 296. For example, the first set of monitor signals may be a set of analog monitor signals transmitted by the monitor circuitry 240 to the ADC circuitry 296, and the second set of monitor signals may be a set of digital monitor signals generated by the ADC circuitry 296 based on the set of analog monitor signals and transmitted by the ADC circuitry 296 to the monitor analysis circuitry 270.

The monitor analysis circuitry 270 may be further configured to: detect a second fault condition based on the second set of monitor signals; in response to detection of the second fault condition, generate a second crowbar trigger activation signal; and transmit the second crowbar trigger activation signal to the crowbar trigger circuitry. The second crowbar trigger activation signal may comprise a digital crowbar trigger activation signal (nMICRO_CROWBAR), any other suitable crowbar trigger activation signal, or any combination thereof.

In some embodiments, the monitor analysis circuitry 270 may be in electrical communication with a set of relays comprised by the HV relay circuitry 222. The monitor analysis circuitry 270 may be further configured to: in response to the detection of the second fault condition, generate a set of relay deactivation signals; and transmit the set of relay deactivation signals to the set of relays. Each relay in the set of relays may be configured to: receive one of the relay deactivation signals in the set of relay deactivation signals from the monitor analysis circuitry; and, in response to receipt of the one of the relay deactivation signals, electrically disconnect the capacitor charge circuitry 216 from the EPE needle circuitry 224.

In some embodiments, the monitor analysis circuitry 270 may comprise HV monitor analysis circuitry 280 and crowbar trigger control signal generation circuitry 282. The HV monitor analysis circuitry 280 may be configured to: receive a second continuously monitored HV voltage signal (digital HV_MON) generated based on the first continuously monitored HV voltage signal, wherein the second set of monitor signals comprises the second continuously monitored HV voltage signal; detect a second HV overvoltage condition (e.g., a digital HV voltage above or equal to 1,512 volts for an HV supply voltage of 1,500 volts) based on the second continuously monitored HV voltage signal, wherein the second fault condition is the second HV overvoltage condition; in response to detection of the second HV overvoltage condition, generate a second HV overvoltage signal; and transmit the second HV overvoltage signal to the crowbar trigger control signal generation circuitry 282. The crowbar trigger control signal generation circuitry 282 may be configured to receive the second HV overvoltage signal from the HV monitor analysis circuitry 280; in response to receipt of the second HV overvoltage signal, generate the second crowbar trigger activation signal (nMICRO_CROWBAR); and transmit the second crowbar trigger activation control signal to the crowbar trigger circuitry 230.

In some embodiments, the monitor analysis circuitry 270 may comprise capacity monitor analysis circuitry 278 and crowbar trigger control signal generation circuitry 282. The capacity monitor analysis circuitry 278 may be configured to: receive a second continuously monitored capacitor voltage signal (digital CAP_MON) generated based on the first continuously monitored capacitor voltage signal, wherein the second set of monitor signals comprises the second continuously monitored capacitor voltage signal; detect a second capacitor overvoltage condition (e.g., a digital capacitor voltage in excess of a digital capacitor voltage overvoltage (digital VAR_CAP_V)) based on the second continuously monitored capacitor voltage signal, wherein the second fault condition is the second capacitor overvoltage condition; in response to detection of the second capacitor overvoltage condition, generate a second capacitor overvoltage signal; and transmit the second capacitor overvoltage signal to the crowbar trigger control signal generation circuitry 282. The crowbar trigger control signal generation circuitry 282 may be configured to: receive the second capacitor overvoltage signal from the capacity monitor analysis circuitry 278; in response to receipt of the second capacitor overvoltage signal, generate the second crowbar trigger activation signal (nMICRO_CROWBAR); and transmit the second crowbar trigger activation control signal to the crowbar trigger circuitry 230.

In some embodiments, the monitor analysis circuitry 270 may comprise pulse monitor analysis circuitry 276 and crowbar trigger control signal generation circuitry 282. The pulse monitor analysis circuitry 276 may be configured to: receive a second continuously monitored pulse voltage signal (digital PULSE_MON) generated based on the first continuously monitored pulse voltage signal, wherein the second set of monitor signals comprises the second continuously monitored pulse voltage signal; detect a second pulse overvoltage condition (e.g., a digital pulse voltage in excess of a digital pulse voltage overvoltage (digital VAR_PULSE_V)) based on the second continuously monitored pulse voltage signal, wherein the second fault condition is the second pulse overvoltage condition; in response to detection of the second pulse overvoltage condition, generate a second pulse overvoltage signal; and transmit the second pulse overvoltage signal to the crowbar trigger control signal generation circuitry 282. The crowbar trigger control signal generation circuitry 282 may be configured to receive the second pulse overvoltage signal from the pulse monitor analysis circuitry 276; in response to receipt of the second pulse overvoltage signal, generate the second crowbar trigger activation signal (nMICRO_CROWBAR); and transmit the crowbar trigger activation control signal to the crowbar trigger circuitry 230.

In some embodiments, the pulse monitor analysis circuitry 276 may be further configured to: determine a rise time of a rising edge of a pulse in the set of pulses; and detect the second pulse overvoltage condition (e.g., a rise time in excess of a predetermined rise time threshold value) based on the rise time. In some embodiments, the pulse monitor analysis circuitry 276 may be further configured to: determine a fall time of a falling edge of a pulse in the set of pulses; and detect the second pulse overvoltage condition (e.g., a fall time in excess of a predetermined fall time threshold value) based on the fall time.

In some embodiments, the monitor analysis circuitry 270 may comprise current monitor analysis circuitry 274 and crowbar trigger control signal generation circuitry 282. The current monitor analysis circuitry 274 may be configured to: receive a second continuously monitored current signal (digital CURRENT_MON) generated based on the first continuously monitored current signal, wherein the second set of monitor signals comprises the second continuously monitored current signal; detect a second overcurrent condition (e.g., a digital current in excess of a digital current overcurrent value) based on the second continuously monitored current signal, wherein the second fault condition is the second overcurrent condition; in response to detection of the second overcurrent condition, generate a second overcurrent signal; and transmit the second overcurrent signal to the crowbar trigger control signal generation circuitry 282. The crowbar trigger control signal generation circuitry 282 may be configured to: receive the second overcurrent signal from the current monitor analysis circuitry 274; in response to receipt of the second overcurrent signal, generate the second crowbar trigger activation signal (nMICRO_CROWBAR); and transmit the second crowbar trigger activation control signal to the crowbar trigger circuitry 230.

In some embodiments, the monitor analysis circuitry 270 may be in electrical communication with the set of relays comprised by the HV relay circuitry 222. The monitor analysis circuitry 270 may comprise impedance monitor analysis circuitry 272. The impedance monitor analysis circuitry 272 may be configured to: receive a second monitored impedance voltage signal (digital IMPEDANCE_MON) generated based on the first monitored impedance voltage signal; detect a second impedance testing fault condition (e.g., a digital resistance less than 20 ohms) based on the second monitored impedance voltage signal; in response to detection of the second monitored impedance voltage signal, generate a second set of relay deactivation signals; and transmit the second set of relay deactivation signals to the set of relays. Each relay in the set of relays may be configured to: receive one of the relay deactivation signals in the second set of relay deactivation signals from the impedance monitor analysis circuitry; and in response to receipt of the one of the relay deactivation signals in the second set of relay deactivation signals, electrically disconnect the capacitor charge circuitry 216 from the EPE needle circuitry 224.

The crowbar trigger circuitry 230 may be in electrical communication with the monitor circuitry 240 and the monitor analysis circuitry 270. The crowbar trigger circuitry 230 may be configured to: receive the first crowbar trigger activation signal from the monitor circuitry 240; receive the second crowbar trigger activation signal from the monitor analysis circuitry 270; and, in response to either receipt of the first crowbar trigger activation signal or receipt of the second crowbar trigger activation signal, electrically disconnect the HV circuitry 210 from the electroporation electrode circuitry 220, such as by electrically disconnecting the capacitor charge circuitry 216 from the electroporation electrode circuitry 220. In some embodiments, the crowbar trigger circuitry 230 may be configured to electrically disconnect the capacitor charge circuitry 216 from the electroporation electrode circuitry 220 within about 10 microseconds of the detection of the first fault condition or the detection of the second fault condition.

The processor 262 may be embodied in a number of different ways and may, for example, include one or more processing devices configured to perform independently. Additionally or alternatively, the processor 262 may include one or more processors configured in tandem via a bus to enable independent execution of instructions, pipelining, multithreading, or a combination thereof. The term "processor" or "processing circuitry" may be understood to include a single core processor, a multi-core processor, multiple processors internal to the apparatus 200, remote or "cloud" processors, or a combination thereof.

In an example embodiment, the processor 262 may be configured to execute instructions stored in the memory 264 or otherwise accessible to the processor 262. Alternatively or additionally, the processor 262 may be configured to execute hard-coded functionality. As such, whether configured by hardware or software methods, or by a combination of hardware with software, the processor 262 may represent an entity (e.g., physically embodied in circuitry) capable of performing operations according to an embodiment of the present disclosure while configured accordingly. As another example, when the processor 262 is embodied as an executor of program code instructions, the instructions may specifically configure the processor to perform the operations described herein when the instructions are executed.

In some embodiments, the processor 262 (and/or coprocessor or any other processing circuitry assisting or otherwise associated with the processor) may be in communication with the memory 264 via a bus for passing information among components of the apparatus. The memory 264 may be non-transitory and may include, for example, one or more volatile and/or non-volatile memories. For example, the memory 264 may be an electronic storage device (e.g., a computer readable storage medium). In another example, the memory 264 may be a non-transitory computer-readable storage medium storing computer-executable program code instructions that, when executed by a computing system, cause the computing system to perform the various operations described herein. The memory 264 may be configured to store information, data, content, signals applications, instructions (e.g., computer-executable program code instructions), or the like, for enabling the apparatus 200 to carry out various functions in accordance with example embodiments of the present disclosure. For example, the memory 264 may be configured to store monitor signals, fault condition (e.g., overvoltage, overcurrent) detection techniques, crowbar trigger control signals (e.g., crowbar trigger activation signals), relay controls, control signals, or any combination or combinations thereof. It will be understood that the memory 264 may be configured to store partially or wholly any electronic information, data, data structures, signals, embodiments, examples, figures, processes, operations, techniques, algorithms, instructions, systems, apparatuses, methods, or computer program products described herein, or any combination thereof.

In some embodiments, the processing circuitry 260 may include input-output circuitry 266 that may, in turn, be in communication with processor 262 to provide output to the user and, in some embodiments, to receive input such as a command provided by the user. The input-output circuitry 266 may comprise a user interface, such as a graphical user interface (GUI), and may include a display that may include a web user interface, a GUI application, a mobile application, a client device, or any other suitable hardware or software. In some embodiments, the input-output circuitry 266 may also include a keyboard, a mouse, a joystick, a display device, a display screen, a touch screen, touch areas, soft keys, a microphone, a speaker, or other input-output mechanisms. The processor 262, input-output circuitry 266 (which may utilize the processor 262), or both may be configured to control one or more functions of one or more user interface elements through computer-executable program code instructions (e.g., software, firmware) stored in a non-transitory computer-readable storage medium (e.g., memory 264). Input-output circuitry 266 is optional and, in some embodiments, the apparatus 200 may not include input-output circuitry. For example, where the apparatus 200 does not interact directly with the user, the apparatus 200 may generate user interface data for display by one or more other devices with which one or more users directly interact and transmit the generated user interface data to one or more of those devices. For example, the apparatus 200, using user interface circuitry 269, may generate user interface data for display by one or more display devices and transmit the generated user interface data to those display devices.

The communications circuitry 268 may be any device or circuitry embodied in either hardware or a combination of hardware and software that is configured to receive or transmit data from or to a network or any other device, circuitry, or module in communication with the apparatus 200. In this regard, the communications circuitry 268 may include, for example, a network interface for enabling communications with a wired or wireless communication network. For example, the communications circuitry 268 may include one or more network interface cards, antennae, buses, switches, routers, modems, and supporting hardware and/or software, or any other device suitable for enabling communications via a network. In some embodiments, the communication interface may include the circuitry for interacting with the antenna(s) to cause transmission of signals via the antenna(s) or to handle receipt of signals received via the antenna(s). These signals may be transmitted or received by the apparatus 200 using any of a number of Internet, Ethernet, cellular, satellite, or wireless technologies, such as IEEE 802.11, Code Division Multiple Access (CDMA), Global System for Mobiles (GSM), Universal Mobile Telecommunications System (UMTS), Long-Term Evolution (LTE), Bluetooth® v1.0 through v5.0, Bluetooth Low Energy (BLE), infrared wireless (e.g., IrDA), ultra-wideband (UWB), induction wireless transmission, Wi-Fi, near field communications (NFC), Worldwide Interoperability for Microwave Access (WiMAX), radio frequency (RF), RFID, or any other suitable technologies.

In some embodiments, communications circuitry 268 may comprise hardware components designed or configured to receive, from a user device, an electronic indication of a pulse duration (e.g., 100 microseconds), voltage level (e.g., 1,500 volts), and EPE needle addressing or switching pattern output by the apparatus 200. In some embodiments, the communications circuitry 268 may receive the electronic indication in response to a user using input-output circuitry 266 to select a pulse duration, voltage level, or EPE needle addressing or switching pattern from a list of pulse durations, voltage levels, or EPE needle addressing or switching patterns displayed in a graphical user interface provided by user interface circuitry 269.

The user interface circuitry 269 includes hardware components designed or configured to receive, process, generate, and transmit data, such as user interface data. For instance, the user interface circuitry 269 includes hardware components designed or configured to generate user interface data based on any embodiment or combination of embodiments described with reference to FIG. 1, FIG. 2, FIG. 3A, FIG. 3B, FIG. 3C, FIG. 3D, FIG. 4A, FIG. 4B, FIG. 4C, FIG. 5A, FIG. 5B, FIG. 5C, FIG. 5D, FIG. 5E, FIG. 5F, FIG. 5G, FIG. 5H, FIG. 5I, FIG. 5J, FIG. 6A, FIG. 6B, FIG. 6C and FIG. 7. In some embodiments, the user interface circuitry 269 may be in communication with a display device (e.g., input-output circuitry 266, a display 116, a user device, or a display device communicatively coupled thereto) and thus configured to transmit the user interface data to the display device. For example, the user interface circuitry 269 may be configured to generate user interface data and transmit the generated user interface data to the input-output circuitry 266, and the input-output circuitry 266 may be configured to receive the user interface data and display the received user interface data on the display 116. In some embodiments, the user interface circuitry 269 may be configured to transmit the user interface data to the communications circuitry 268, and the communications circuitry 268 may be configured to transmit the user interface data to a user device.

In some embodiments, each of the user interface circuitry 269, impedance monitor analysis circuitry 272, current monitor analysis circuitry 274, pulse monitor analysis circuitry 276, capacity monitor analysis circuitry 278, HV monitor analysis circuitry 280, and crowbar trigger control signal generation circuitry 282 may include a separate processor, specially configured field programmable gate array (FPGA), application specific interface circuit (ASIC), or cloud utility to perform the above functions. In some embodiments, the hardware components described above with reference to user interface circuitry 269, impedance monitor analysis circuitry 272, current monitor analysis circuitry 274, pulse monitor analysis circuitry 276, capacity monitor analysis circuitry 278, HV monitor analysis circuitry 280, and crowbar trigger control signal generation circuitry 282, may, for instance, utilize communications circuitry 268 or any suitable wired or wireless communications path to communicate with a user device, each other, or any other suitable circuitry or device.

In some embodiments, one or more of the user interface circuitry 269, impedance monitor analysis circuitry 272, current monitor analysis circuitry 274, pulse monitor analysis circuitry 276, capacity monitor analysis circuitry 278, HV monitor analysis circuitry 280, and crowbar trigger control signal generation circuitry 282 may be hosted locally by the apparatus 200. In some embodiments, one or more of the user interface circuitry 269, impedance monitor analysis circuitry 272, current monitor analysis circuitry 274, pulse monitor analysis circuitry 276, capacity monitor analysis circuitry 278, HV monitor analysis circuitry 280, and crowbar trigger control signal generation circuitry 282 (e.g., by one or more cloud servers) and thus need not physically reside on the apparatus 200. Thus, some or all of the functionality described herein may be provided by a remote circuitry. For example, the apparatus 200 may access one or more remote circuitries via any sort of networked connection that facilitates transmission of data and electronic information between the apparatus 200 and the remote circuitries. In turn, the apparatus 200 may be in remote communication with one or more of the user interface circuitry 269, impedance monitor analysis circuitry 272, current monitor analysis circuitry 274, pulse monitor analysis circuitry 276, capacity monitor analysis circuitry 278, HV monitor analysis circuitry 280, and crowbar trigger control signal generation circuitry 282.

As described above and as will be appreciated based on this disclosure, embodiments of the present disclosure may be configured as systems, apparatuses, methods, mobile devices, backend network devices, computer program products, other suitable devices, and combinations thereof. Accordingly, embodiments may comprise various means including any combination of software with hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices. As will be appreciated, any computer program instructions and/or other type of code described herein may be loaded onto a computer, processor or other programmable apparatus's circuitry to produce a machine, such that the computer, processor, or other programmable circuitry that executes the code on the machine creates the means for implementing various functions, including those described herein.

The user device may be embodied by one or more computing devices or systems that also may include processing circuitry, memory, input-output circuitry, and communications circuitry. For example, a user device may be a laptop computer on which an app (e.g., a GUI application) is running or otherwise being executed by processing circuitry. In yet another example, a user device may be a smartphone on which an app (e.g., a webpage browsing app) is running or otherwise being executed by processing circuitry. As it relates to operations described in the present disclosure, the functioning of these devices may utilize components similar to the similarly named components described above with respect to FIG. 2. Additional description of the mechanics of these components is omitted for the sake of brevity. These device elements, operating together, provide the respective computing systems with the functionality necessary to facilitate the communication of data with the EPT treatment instrument described herein.

Having described specific components of example devices involved in the present disclosure, example procedures for detecting fault conditions are described below in connection with FIG. 3A, FIG. 3B, FIG. 3C, FIG. 3D, FIG. 4A, FIG. 4B, FIG. 4C, FIG. 5A, FIG. 5B, FIG. 5C, FIG. 5D, FIG. 5E, FIG. 5F, FIG. 5G, FIG. 5H, FIG. 5I, FIG. 5J, FIG. 6A, FIG. 6B, FIG. 6C and FIG. 7.

Figure 3A:
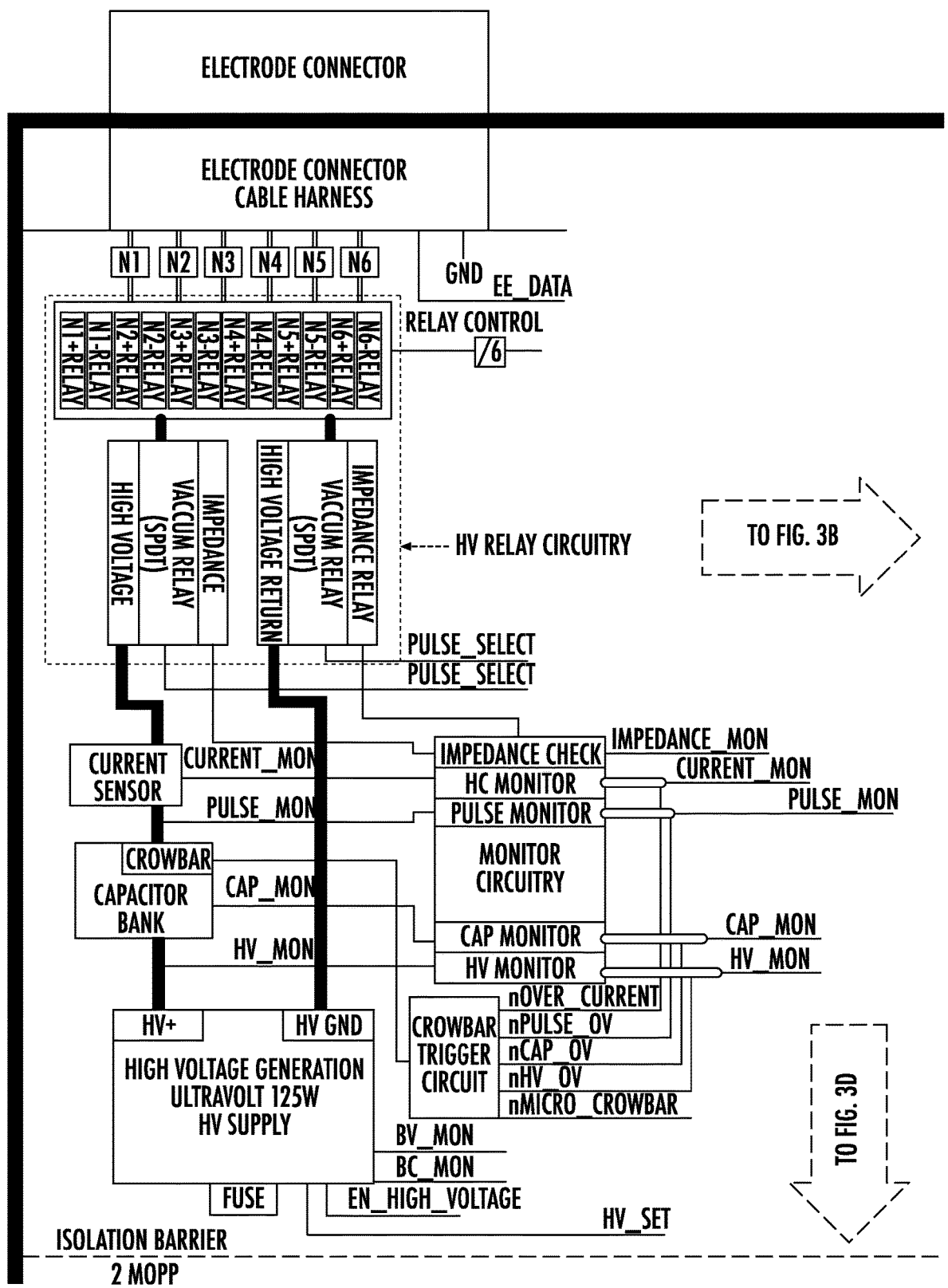
FIGS. 3A, FIG. 3B, FIG. 3C, and FIG. 3D illustrate example block diagrams for an EPT treatment instrument in accordance with some example embodiments described herein.
Figure 3B:
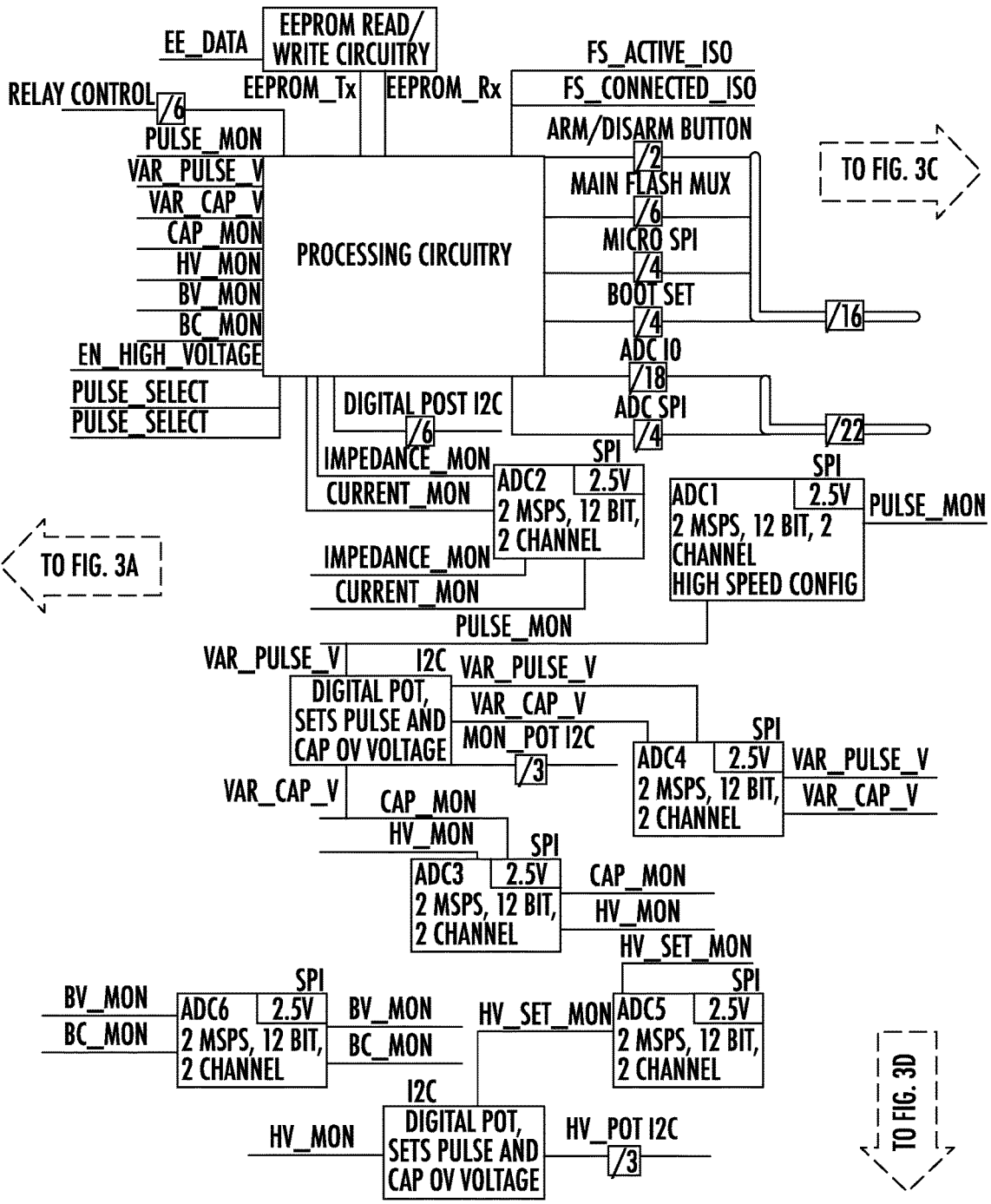
Figure 3C:
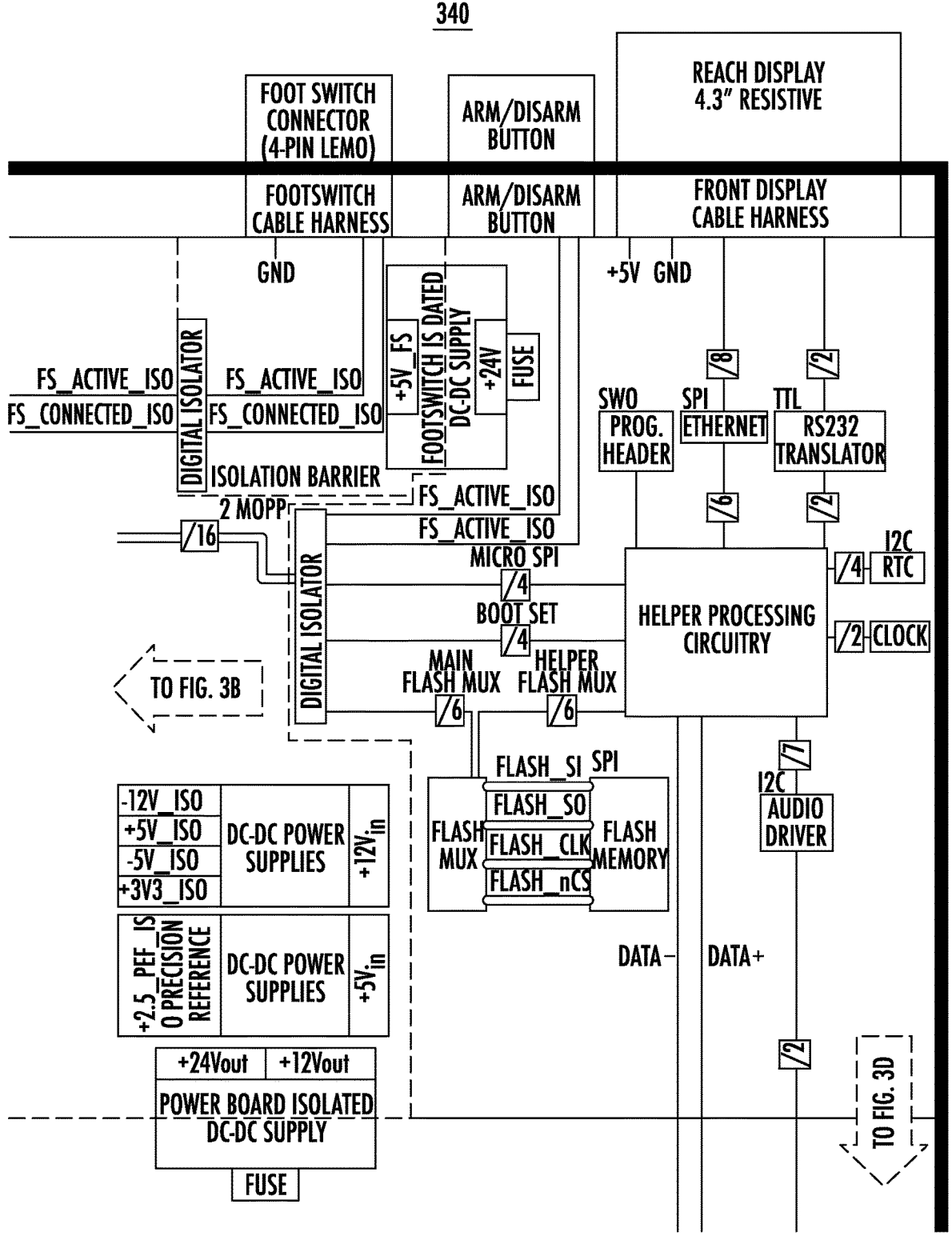
Figure 3D:
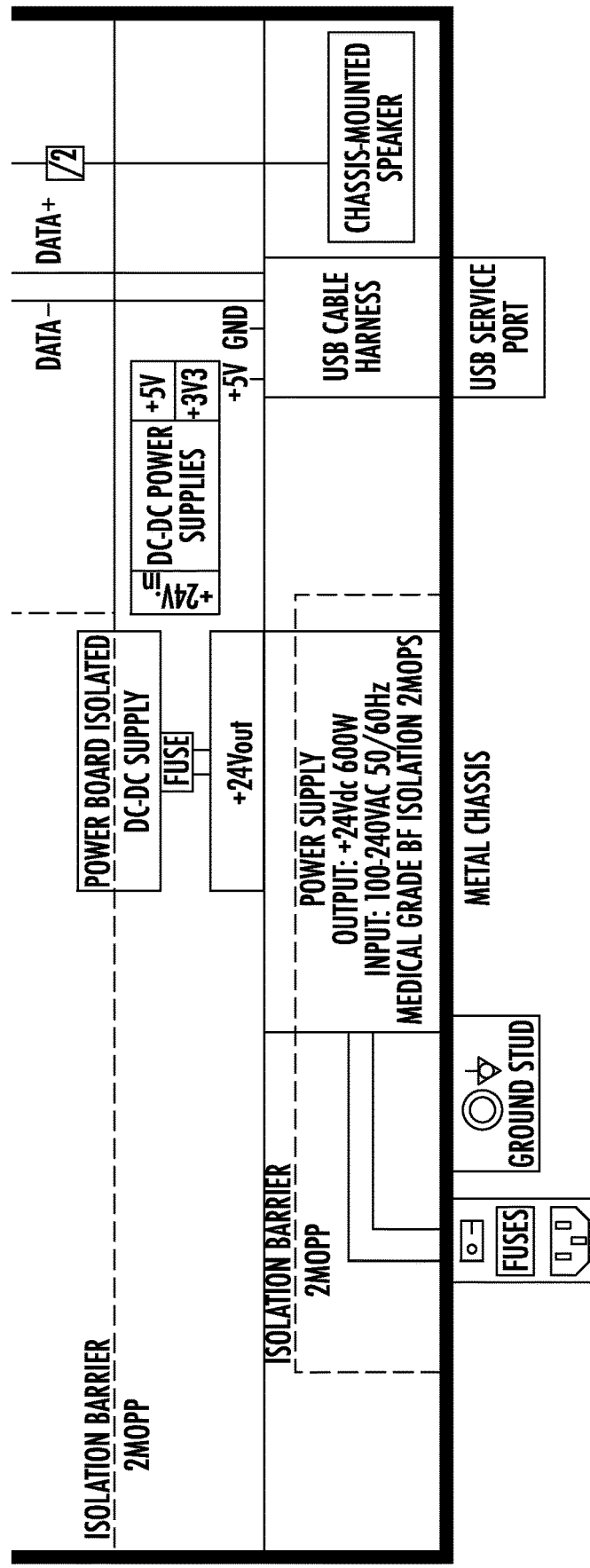

FIG. 3A, FIG. 3B, FIG. 3C, FIG. 3D illustrate example block diagrams for an EPT treatment instrument in accordance with some example embodiments described herein. As shown in FIG. 3A, block diagram 300 comprises components that illustrate, in some instances, an implementation of HV circuitry 210, EPE circuitry 220, crowbar trigger circuitry 230, and monitor circuitry 240. As shown in FIG. 3B, block diagram 320 comprises components that illustrate, in some instances, an implementation of processing circuitry 260, control circuitry 290, and ADC circuitry 296. As shown in FIG. 3C, block diagram 340 comprises components that illustrate, in some instances, an implementation of additional processing circuitry and input-output circuitry. As shown in FIG. 3D, block diagram 360 comprises components that illustrate, in some instances, an implementation of additional power generation circuitry and input-output circuitry.

Figure 4A:
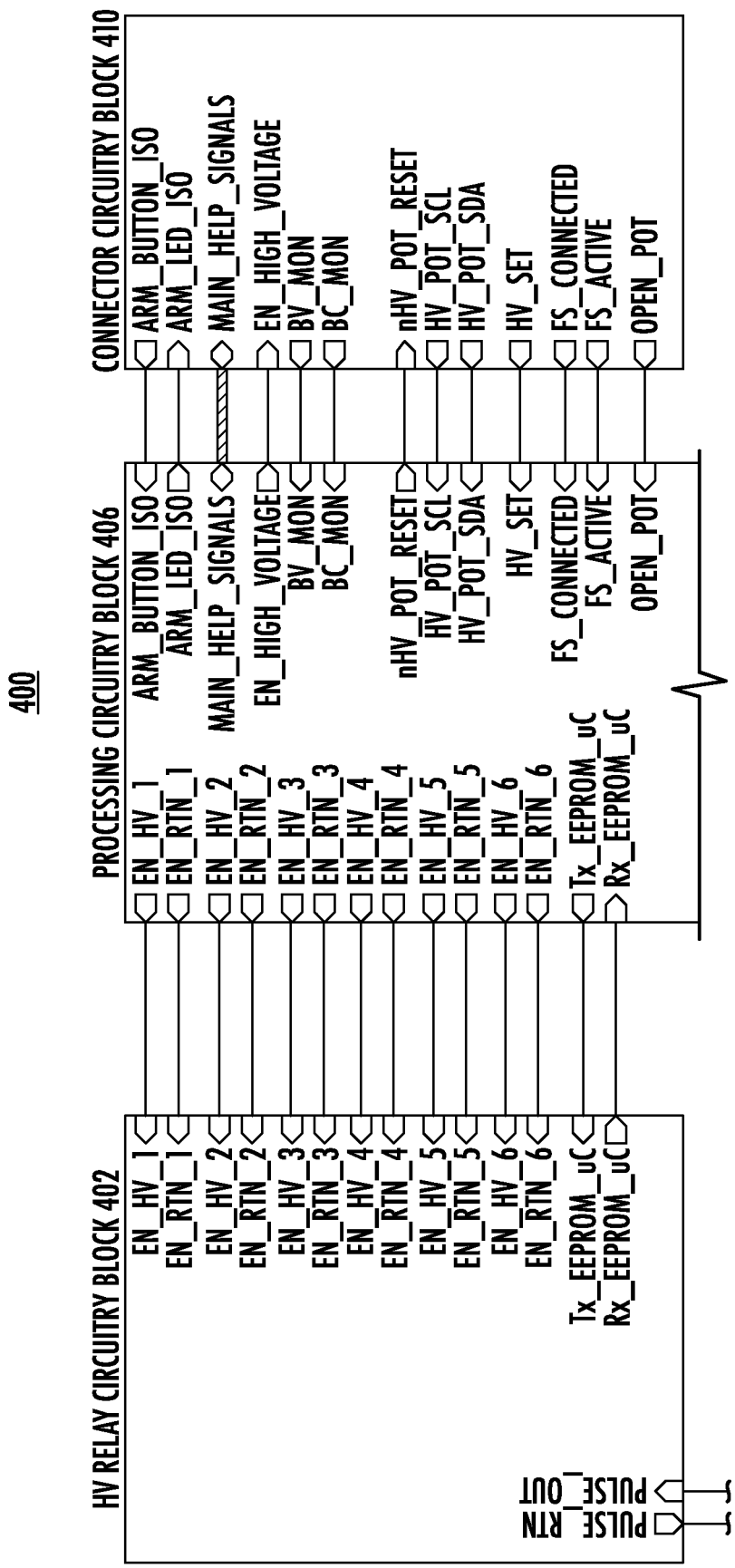
FIGS. 4A, FIG. 4B, and FIG. 4C illustrate example circuitry block diagrams in accordance with some example embodiments described herein.
Figure 4B:
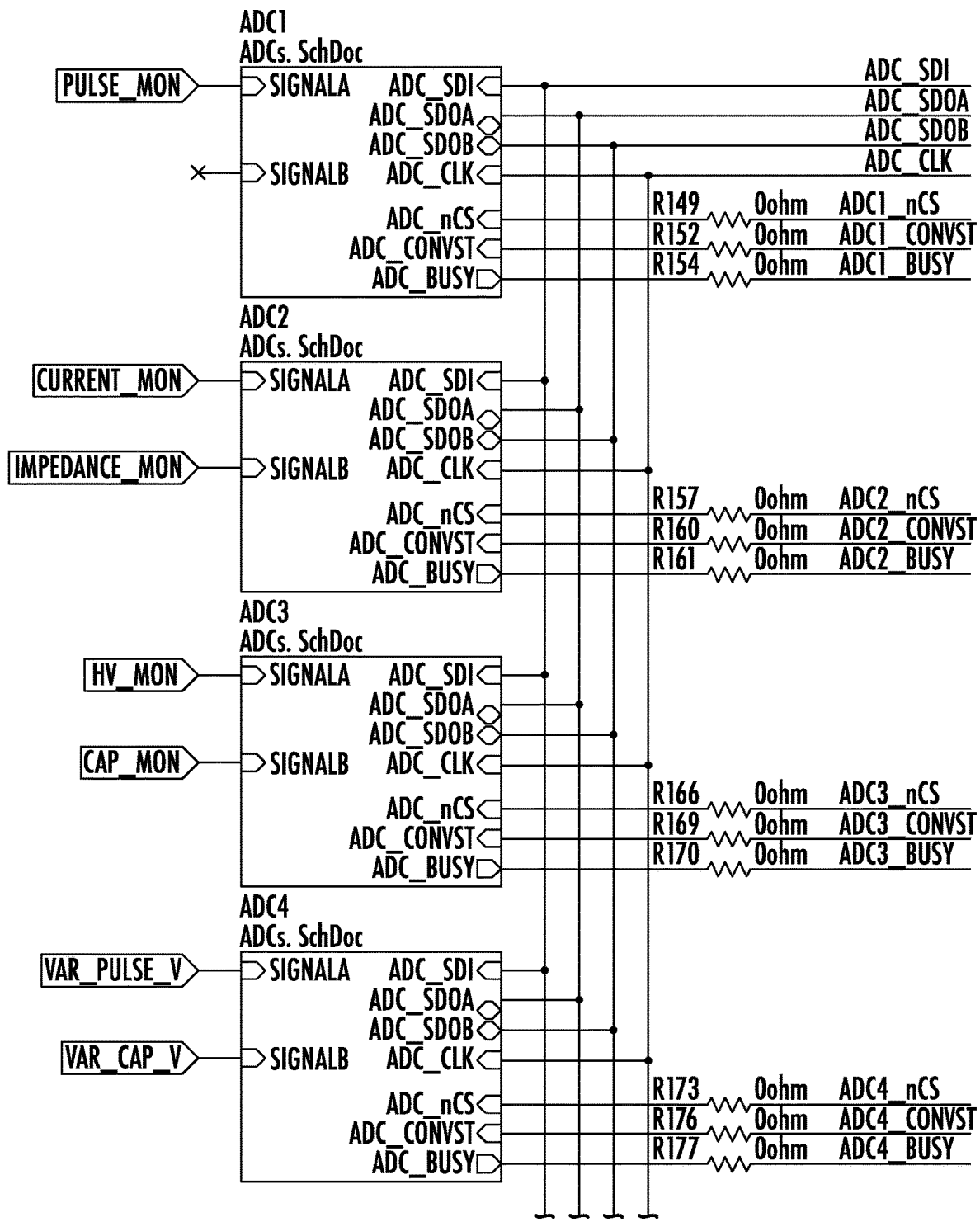
Figure 4C:
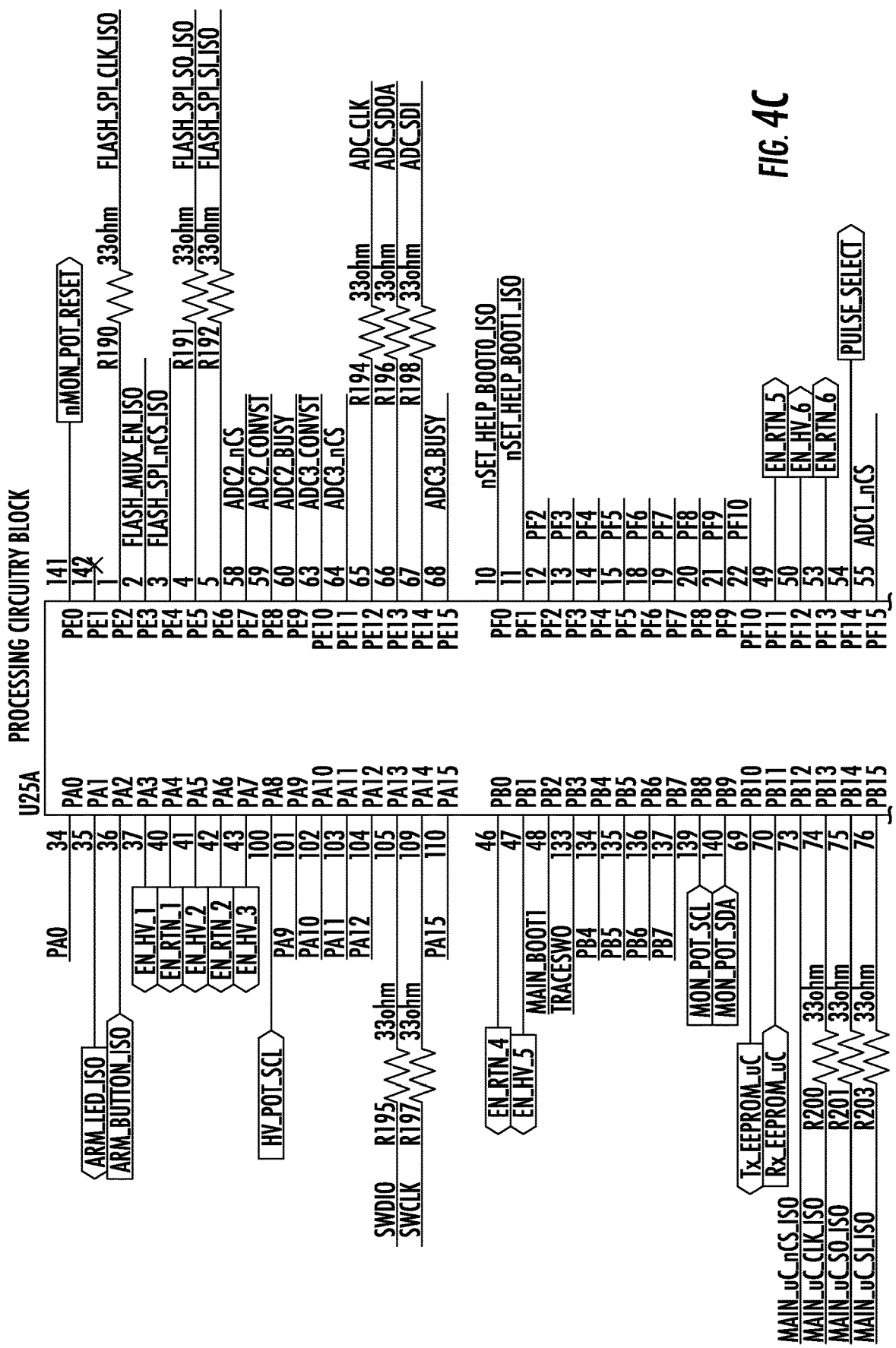

FIG. 4A, FIG. 4B, and FIG. 4C illustrate example circuitry block diagrams in accordance with some example embodiments described herein. As shown in FIG. 4A, circuitry block diagram 400 comprises HV relay circuitry block 402 (e.g., showing signals received and transmitted by HV relay circuitry 222), monitor circuitry block 404 (e.g., showing signals received and transmitted by monitor circuitry 240), processing circuitry block 406 (e.g., showing signals received and transmitted by processing circuitry 260), and connector circuitry block 410 (e.g., showing signals received and transmitted by HV circuitry 210, HV supply monitor circuitry 252, and control circuitry 290, among others). As further shown in FIG. 4A, processing circuitry block 406 may comprise monitor analysis circuitry block 408 (e.g., showing signals received and transmitted by monitor analysis circuitry 270).

As shown in FIG. 4B, circuitry block diagram 420 comprises a plurality of signal monitoring blocks (e.g., showing signals received and transmitted by ADC circuitry 296).

In some embodiments, each of the 0 ohm resistors shown in FIG. 4B may be placed as close to a 30 position connector as possible.

As shown in FIG. 4C, circuitry block diagram 440 comprises a processing circuitry block (e.g., showing signals received and transmitted by processing circuitry 260). In some embodiments, the component Y1 may be placed as close to the processing circuitry block as possible. In some embodiments, processing circuitry 260 may be implemented, in part or in whole, as the processing circuitry block shown in FIG. 4C.

Figure 5A:
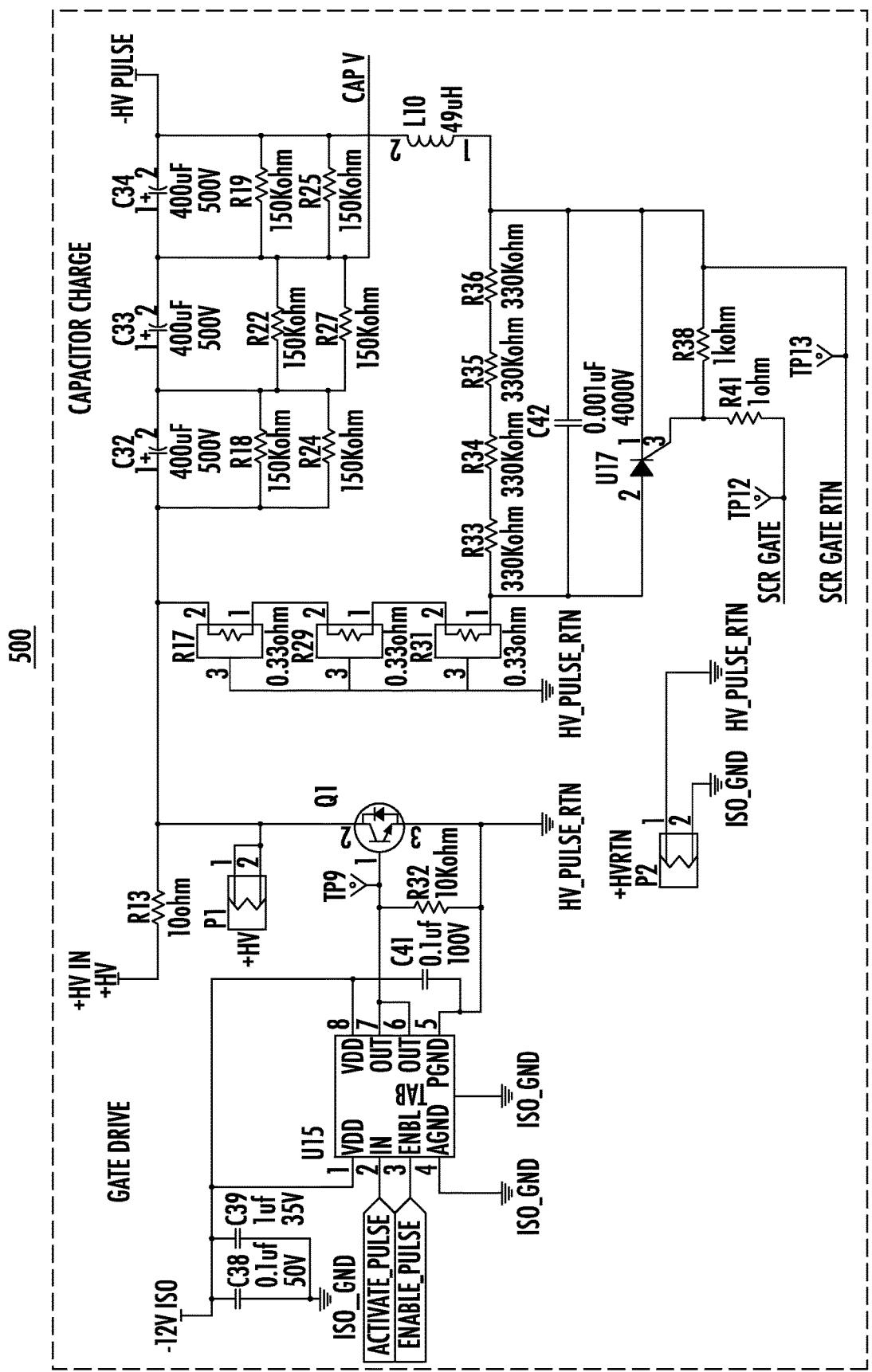

FIG. 5A, FIG. 5B, FIG. 5C, FIG. 5D, FIG. 5E, FIG. 5F, FIG. 5G, FIG. 5H, FIG. 5I, and FIG. 5J illustrate example schematic diagrams in accordance with some example embodiments described herein. As shown in FIG. 5A, circuitry 500 comprises gate drive circuitry and capacitor charge circuitry. In some embodiments, gate drive circuitry 214 and capacitor charge circuitry 216 may be implemented, in part or in whole, as circuitry 500. In some embodiments, the AGND and PGND terminals of component U15 are configured to be connected by a single thick trace directly under component U15. In some embodiments, the component Q1 is disposed to allow space for a heatsink, such as a clip on heatsink. In some embodiments, the HV lines are configured to carry up to 90 amps of current.

Figure 5B:
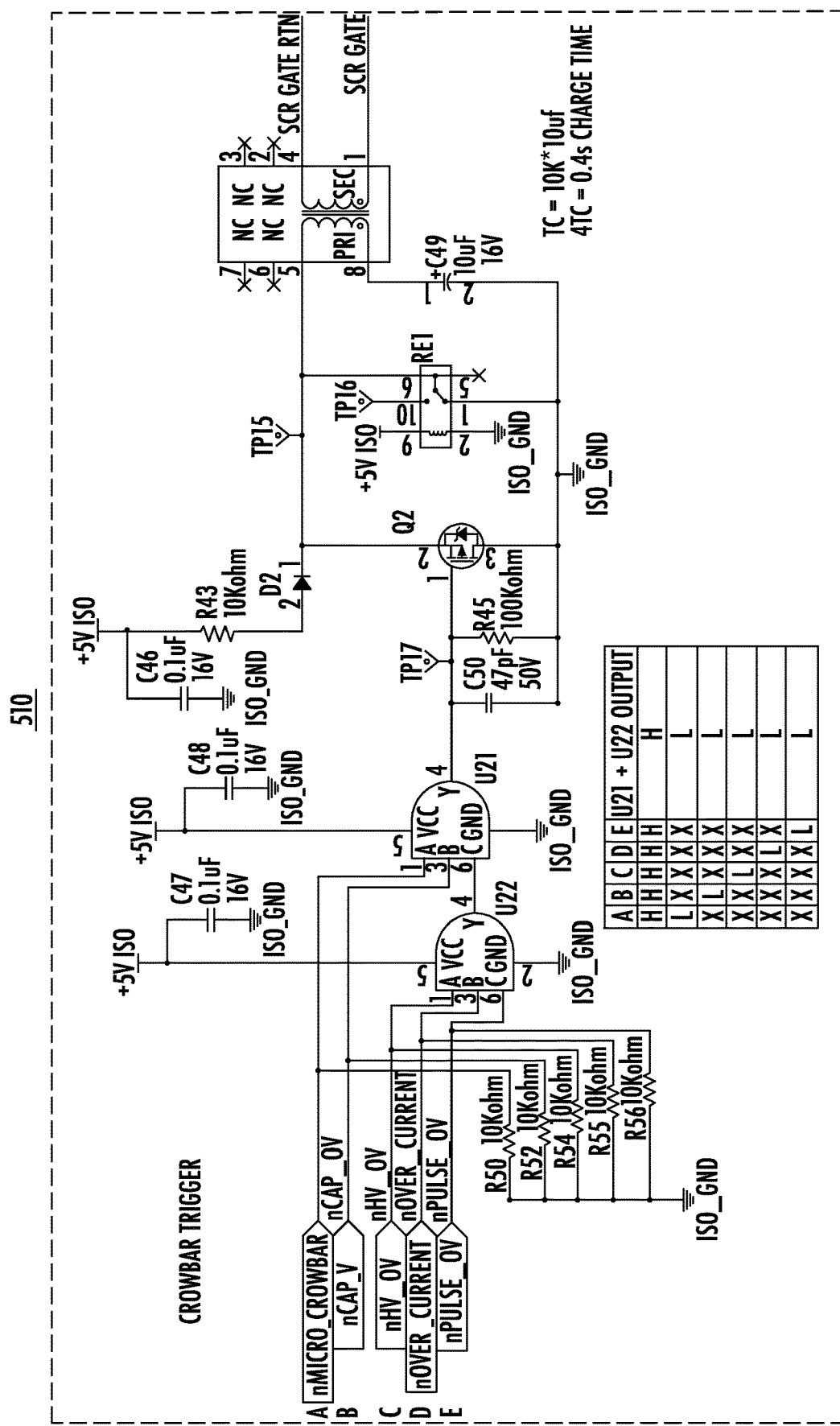

As shown in FIG. 5B, circuitry 510 comprises crowbar trigger circuitry. In some embodiments, crowbar trigger circuitry 230 may be implemented, in part or in whole, as circuitry 510. In some embodiments, the crowbar trigger circuitry may use AND gates to receive signals from microcontrollers (e.g., processing circuitry 260) and analog components. In some embodiments, the high state of U21+U22 is normal operation; the low state of U21+U22 transmits a crowbar activation signal.

In one illustrative example embodiment, the crowbar trigger circuitry capacitor C49 is configured to be shorted by relay REI, causing a 5V signal to be generated by transformer T1 across the capacitor charge circuitry signals SCR_GATE and SCR_GATE_RTN electrically coupled to circuitry 500 shown in FIG. 5A. This generated 5V signal is applied at the gate of silicon controlled rectifier (SCR) U17 of circuitry 500 shown in FIG. 5A, which brings component U17 into forward conduction mode, bypassing resistors R33, R34, R35, and R36. As a result, the +HV line is pulled to zero while all the charge on the HV capacitors C32, C33, and C34 flows through series resistors R17, R29, and R31. Additionally, when -HV_PULSE goes from 0 to −1300 Vdc, the inductor L10 reverses polarity and mitigates the ensuing rush of current. The majority of the current passes through high-wattage resistors R17, R29, and R31, which are also adjusted to alter the rate of decay of voltage.

In another illustrative example embodiment, circuitry 510 becomes enabled on power-up when the +5V_ISO rail charges capacitor C49. When an active-low signal is induced on one of the 5 inputs (nMICRO_CROWBAR, nCAP_OV, nHV_OV, nOVER_CURRENT, and nPULSE_OV), the gate of component Q2 becomes low turning on the PMOS. The capacitor C49 discharges through component Q2, sending a pulse through transformer T1 to the gate of SCR U17. Once the gate of the SCR receives a signal it becomes forward biased, allowing any energy stored in the HV capacitors C32, C33, and C34 to discharge. This energy is dissipated through resistors R17, R29, and R31 with inducer L10 limiting current spikes. On the event that the HV capacitors C32, C33, and C34 are charged and the system experiences a power failure, relay RE13 (e.g., relay RE13 is substantially similar to relay RE5 coupled to EPE Needle 1 shown in FIG. 5J, but is coupled to EPE Needle 6 rather than EPE Needle 1) will close allowing capacitor C49 to discharge and activating the circuitry 510 as disclosed above.

In some embodiments, by including hardware-based crowbar trigger inputs (e.g., nCAP_OV, nHV_OV, nOVER_CURRENT, nPULSE_OV) in addition to a software-based crowbar trigger input (e.g., nMICRO_CROWBAR), the circuitry 510 may react more quickly to any monitored conditions (e.g., voltage, capacitance, current, pulse) which go out-of-specification than typical processor-based EPT treatment systems due to the inherent latencies in processor-based signal changes. In some embodiments, the circuitry 510 is configured to initiate the termination of the delivery of a therapeutic voltage pulse in less than 10 microseconds, following the identification of a fault condition. Accordingly, circuitry 510 is able to truncate not only a therapy sequence, but also an individual therapy pulse, thereby increasing the inherent patient safety of the EPT treatment instrument.

Figure 5C:
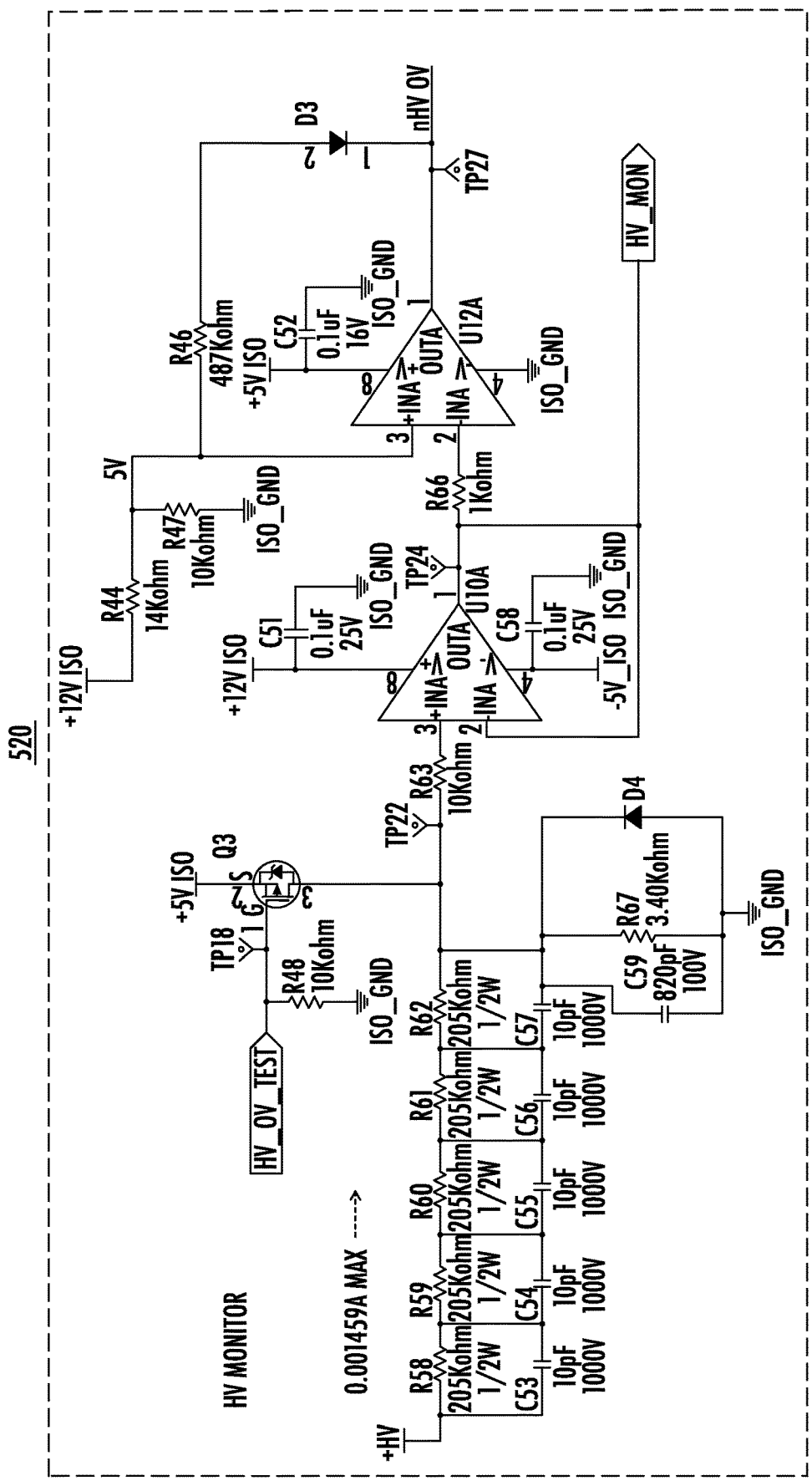

As shown in FIG. 5C, circuitry 520 comprises HV monitor circuitry. In some embodiments, HV monitor circuitry 250 may be implemented, in part or in whole, as circuitry 520. In some embodiments, circuitry 520 is configured to receive an input +HV between 0 volts and 1,500 volts, and generate an output HV_MON between 0 volts and 4.983 volts. In some embodiments, HV_OV is set to 1,500 volts, and 5 volts VCC sets the trigger for 1,512 volts. In some embodiments, HV_MON=(3.4K/(3.4K+1.025M))*HV+ 4.983V=0.003306 Ohms*1500V.

Figure 5D:
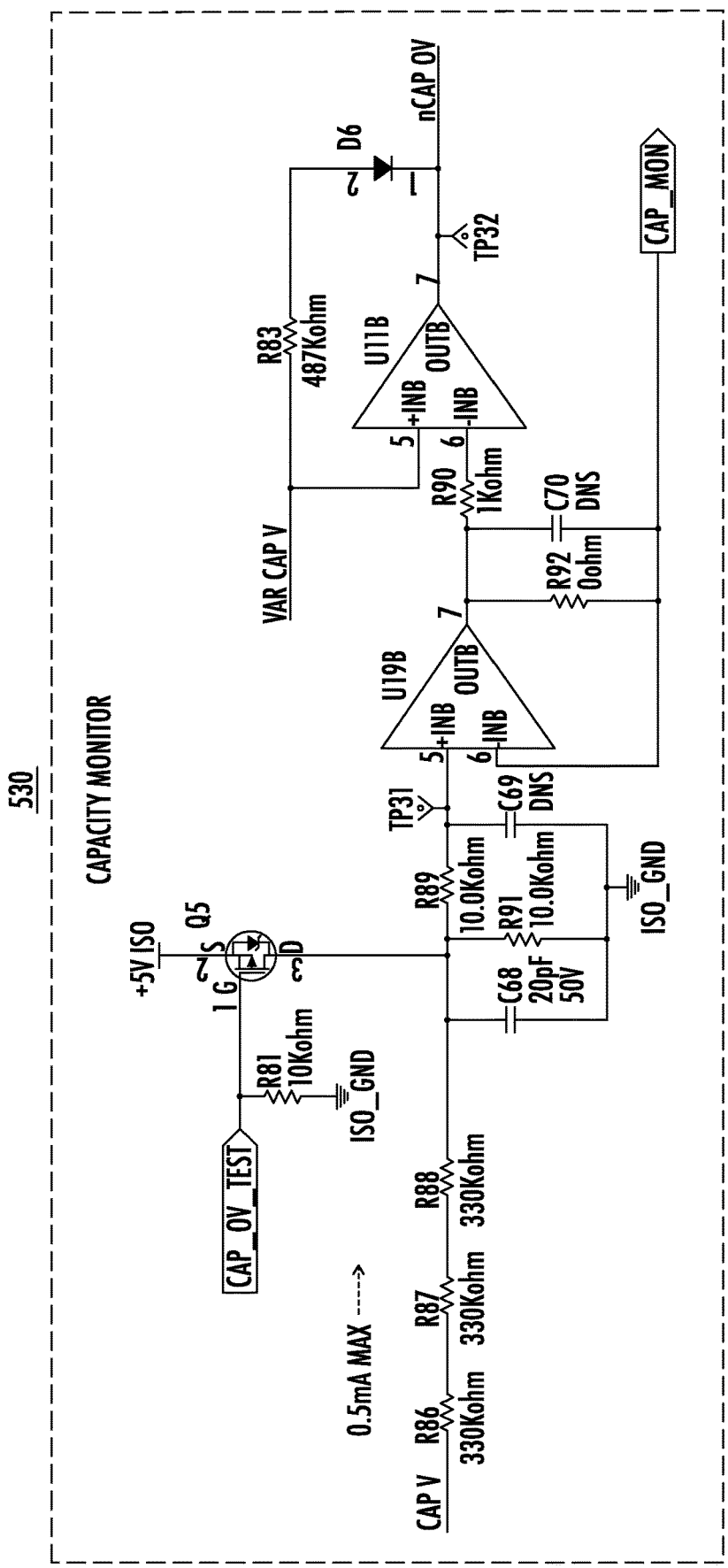

As shown in FIG. 5D, circuitry 530 comprises capacity monitor circuitry. In some embodiments, capacity monitor circuitry 248 may be implemented, in part or in whole, as circuitry 530. In some embodiments, circuitry 530 is configured to receive an input CAP_V between 0 volts and 500 volts, where +HV is between 0 volts and 1,500 volts. In some embodiments, CAP_V=0.33*HV+. In some embodiments, CAP_MON=(10K/(10K+990K))*CAP_V; 5V=0.01 Ohms*CAP_V; and 5V=0.00333*HV+.

Figure 5E:
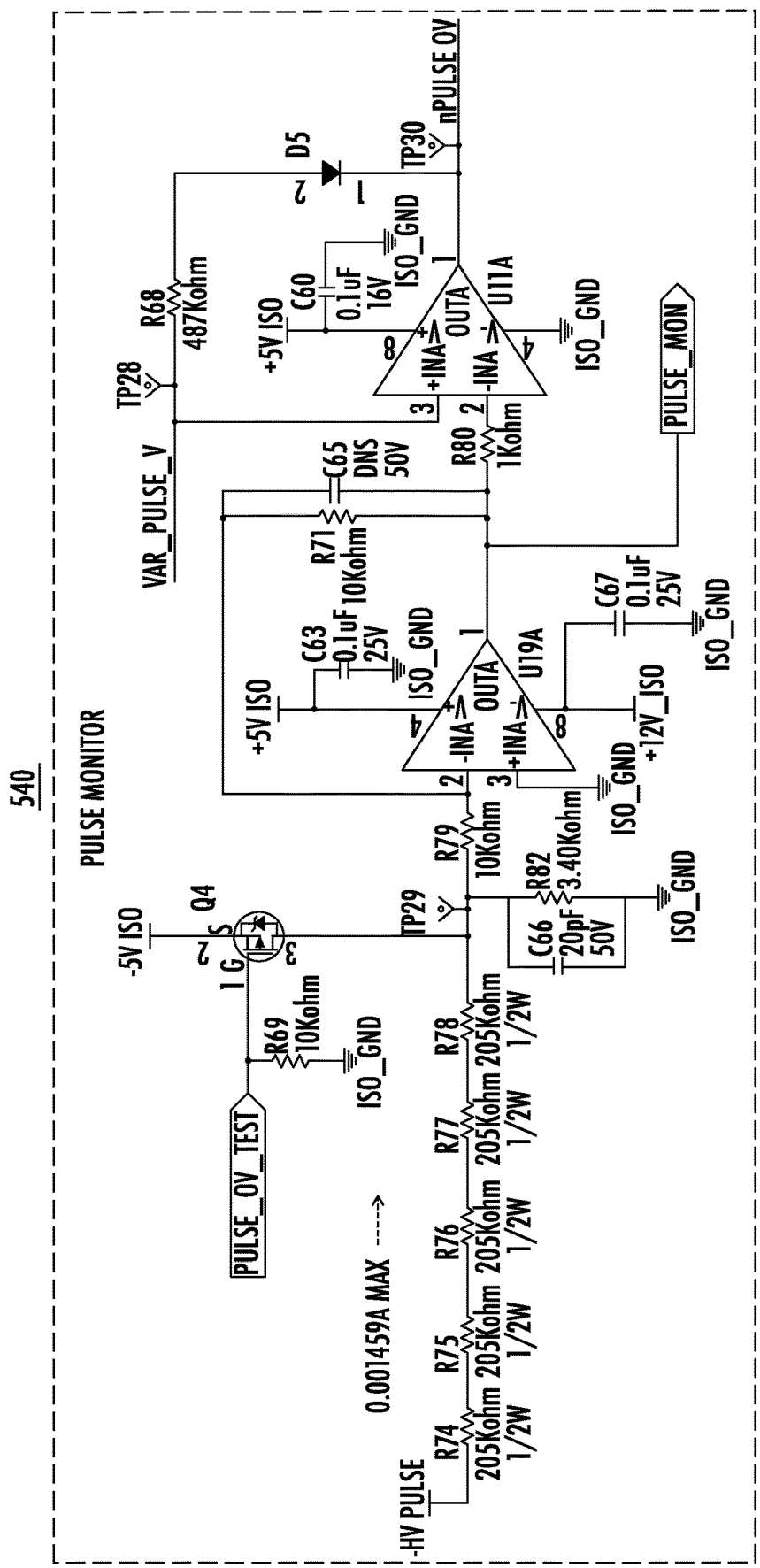

As shown in FIG. 5E, circuitry 540 comprises pulse monitor circuitry. In some embodiments, pulse monitor circuitry 246 may be implemented, in part or in whole, as circuitry 540. In some embodiments, circuitry 540 is configured to receive an input −HV_Pulse between 0 volts and −1,500 volts, and generate an output PULSE_MON between 0 volts and 4.983 volts. In some embodiments, PULSE_MON=(3.4K/(3.4K+1.025M))*HV_PULSE; and (Inverted) 4.983V=0.003306 Ohms*(−1500V).

Figure 5F:
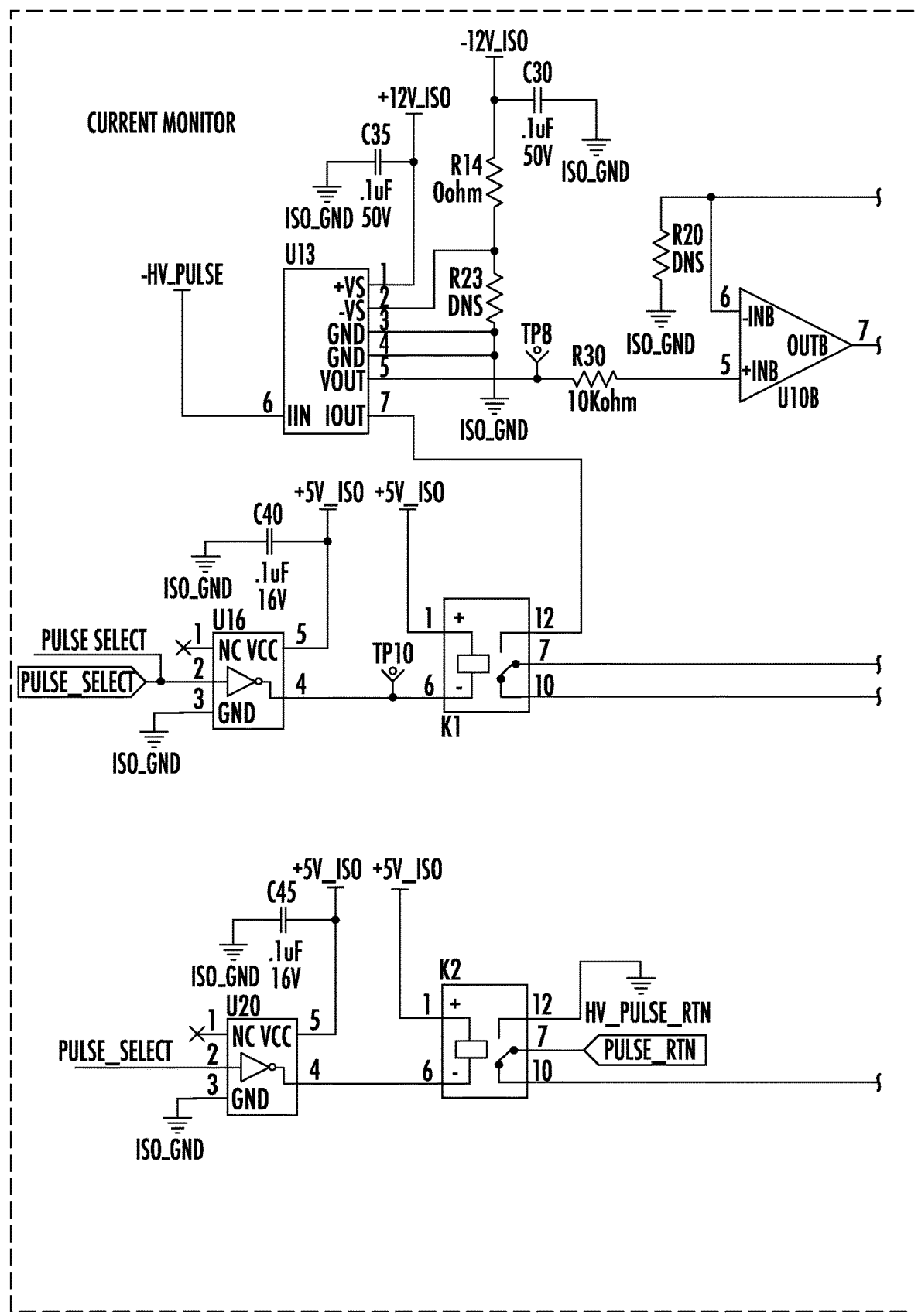

As shown in FIG. 5F, circuitry 550 comprises current monitor circuitry and impedance monitor circuitry. In some embodiments, current monitor circuitry 244 and impedance monitor circuitry 242 may be implemented, in part or in whole, as circuitry 550. In some embodiments, the measured tissue resistance that will result in the detection of a fault condition is between 0 Ohms and 20 Ohms. In some embodiments, IMPEDANCE_MON is between 4.1667 volts and 4.1528 volts. In some embodiments, an ADC electrically coupled to circuitry 550, such as ADC2 shown in FIG. 3B, is configured to detect 11 steps between the difference of 0.0138V. In some embodiments, OPEN=0V; and 10K Skin Resistance=1.5625V.

In some embodiments, the K1 and K2 relays shown in FIG. 5F may be configured to switch between test pulses and therapy pulses/impedance monitoring and ground to separate low voltage and high voltage circuit modes. For example, when the K1 and K2 relays are switched to node 12, the circuitry 550 is in therapy pulse mode. In another example, when the K1 and K2 relays are switched to 10, the circuitry 550 is in impedance testing mode. In some embodiments, the LV impedance check is terminated when a fault is detected by executing a single software function. In some embodiments, a single software function is executed whenever any fault condition is detected, including a fault detected during an LV impedance check. That single software function performs the following actions, in the order listed: (1) prevent (or truncate) a therapy pulse from being delivered by de-asserting ENABLE_PULSE; (2) disable the HV power supply by de-asserting EN_HIGH VOLTAGE; (3) activate the crowbar trigger by de-asserting nMICRO_CROWBAR; (4) open all "needle output" relays (REI to RE12) by de-asserting EN_HV_1 to EN_HV_6 and EN_RTN_1 to EN_RTN_6; (5) turn off the ARM button LED by de-asserting ARM_LED_ISO; (6) wait for the high voltage circuit to be drained to a voltage of less than 200 Vdc by polling HV_MON; (7) reset the software-controlled crowbar trigger input by asserting nMICRO_CROWBAR; (8) set the identified fault active; and (9) transition to the software "Fault" state.

Figure 5G:
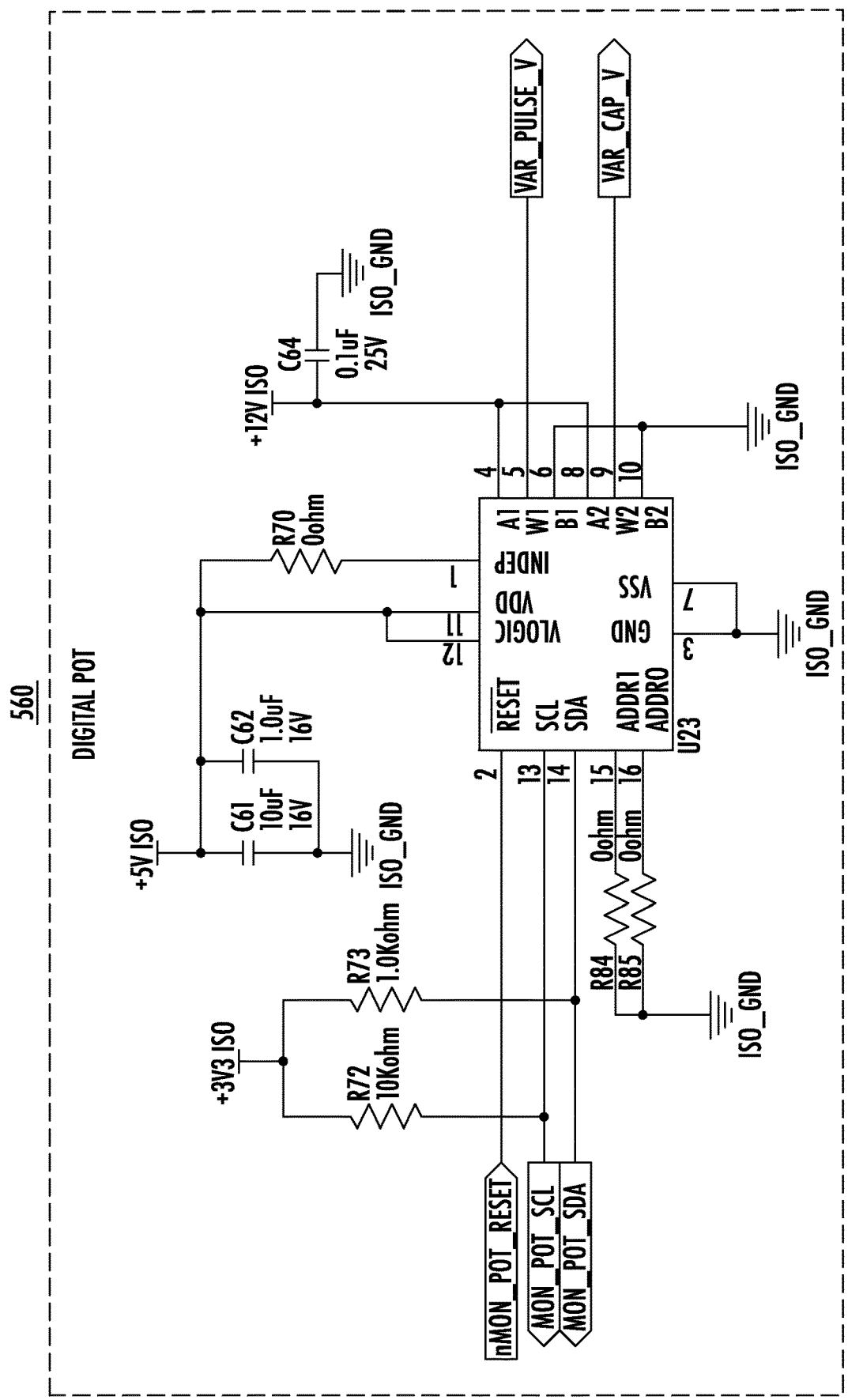

As shown in FIG. 5G, circuitry 560 comprises digital potentiometer (pot) circuitry. In some embodiments, digital pot circuitry 292 may be implemented, in part or in whole, as circuitry 560. In some embodiments, circuitry 560 may be configured to provide the voltage limit via a voltage divider-programmed voltage output which is compared to the pulse and capacitor voltages via op-amps U11A and U11B, allowing the crowbar trigger circuitry (e.g., circuitry 510) to activate in the case that the voltage limit has been exceeded. The outputs of the voltage dividers are VAR_PULSE_V and VAR_CAP_V, which are programmed to represent the pulse and capacitance overvoltage limits, respectively, that activate the crowbar trigger circuitry. The outputs are compared to the monitored signals PULSE_MON and CAP_MON, respectively. If the non-inverting input is greater than the inverting input (PULSE_MON), then the output nPULSE is +Vcc. nPULSE is now high and crowbar trigger circuitry is activated. Feedback is disabled by D5. PULSE_MON must drive above VAR_PULSE_V in order to switch the output to −Vcc. If the non-inverting input is less than PULSE_MON, then the output nPULSE is −Vcc, or ISO GND. With the resistor R68 now in parallel with Rwb (the lower leg of the voltage divider), the non-inverting input reduces from VAR_PULSE_V to a lower threshold voltage VL. Now PULSE_MON must drive below VL to cause the output to switch back to +Vcc. The effect of the diode is to add hysteresis when transitioning from the fault state to the normal state to account for transient signal spikes, and to remove hysteresis during normal operation for safety reasons. In some embodiments, the ADDR1 and ADDR0 pins of component U23 are connected to GND, which sets the I2C address to 0101111. In some embodiments, Rwb=(D/256)*Rab+55; 1108=(D/256)*10000+55; D=27; HEX Number for the program=0x001B. In one illustrative example embodiment, for a 400V applicator, the trip voltage is 1.33V (see capacity monitor, circuitry 530); VAR_CAP_V=1.33V; 1.33V=(12*Rwb)/(10,000 KOhm); Rwb=1108 Ohms; and Raw=10,000−1108=8892 Ohms.

Figure 5H:
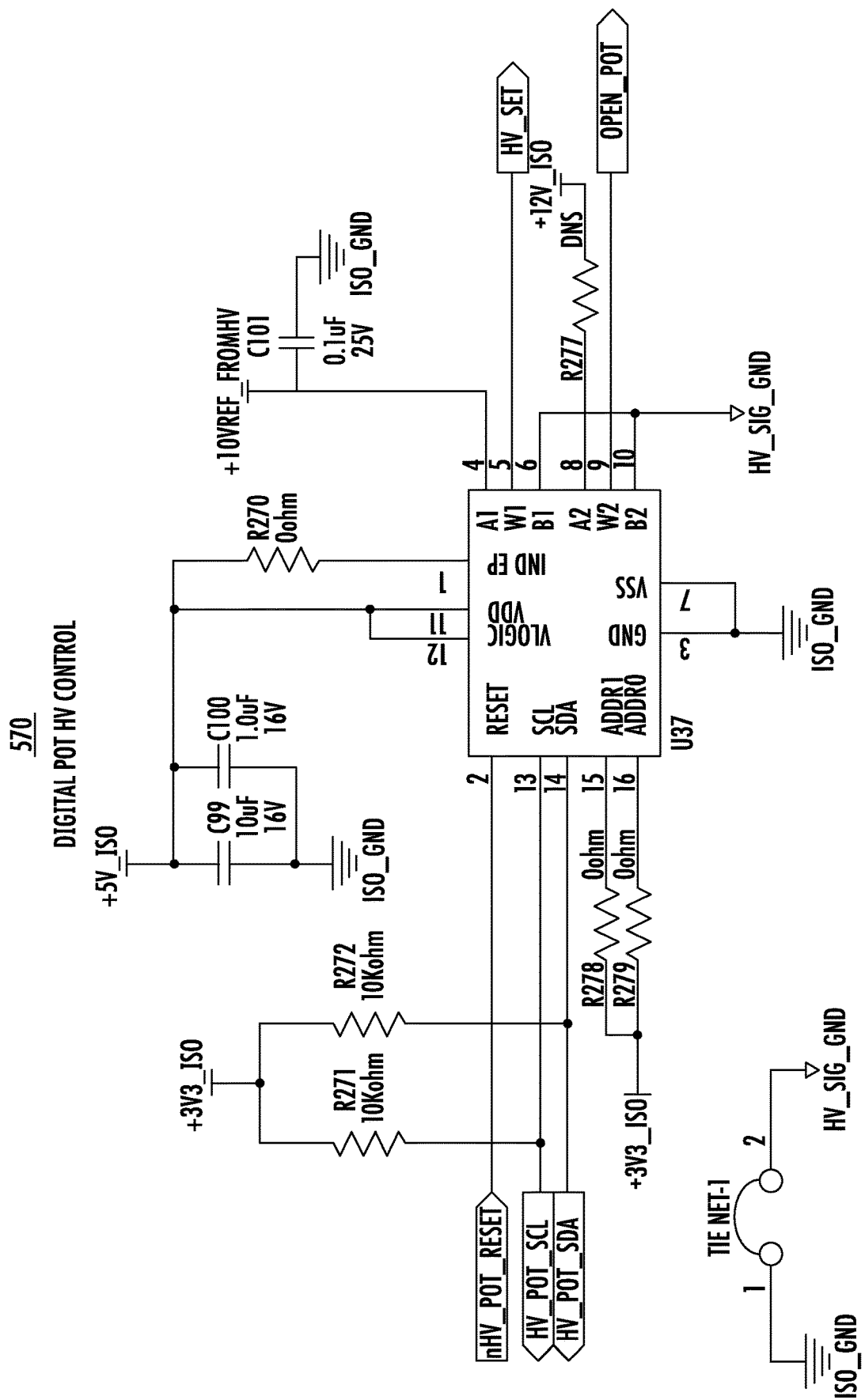
Figure 51:
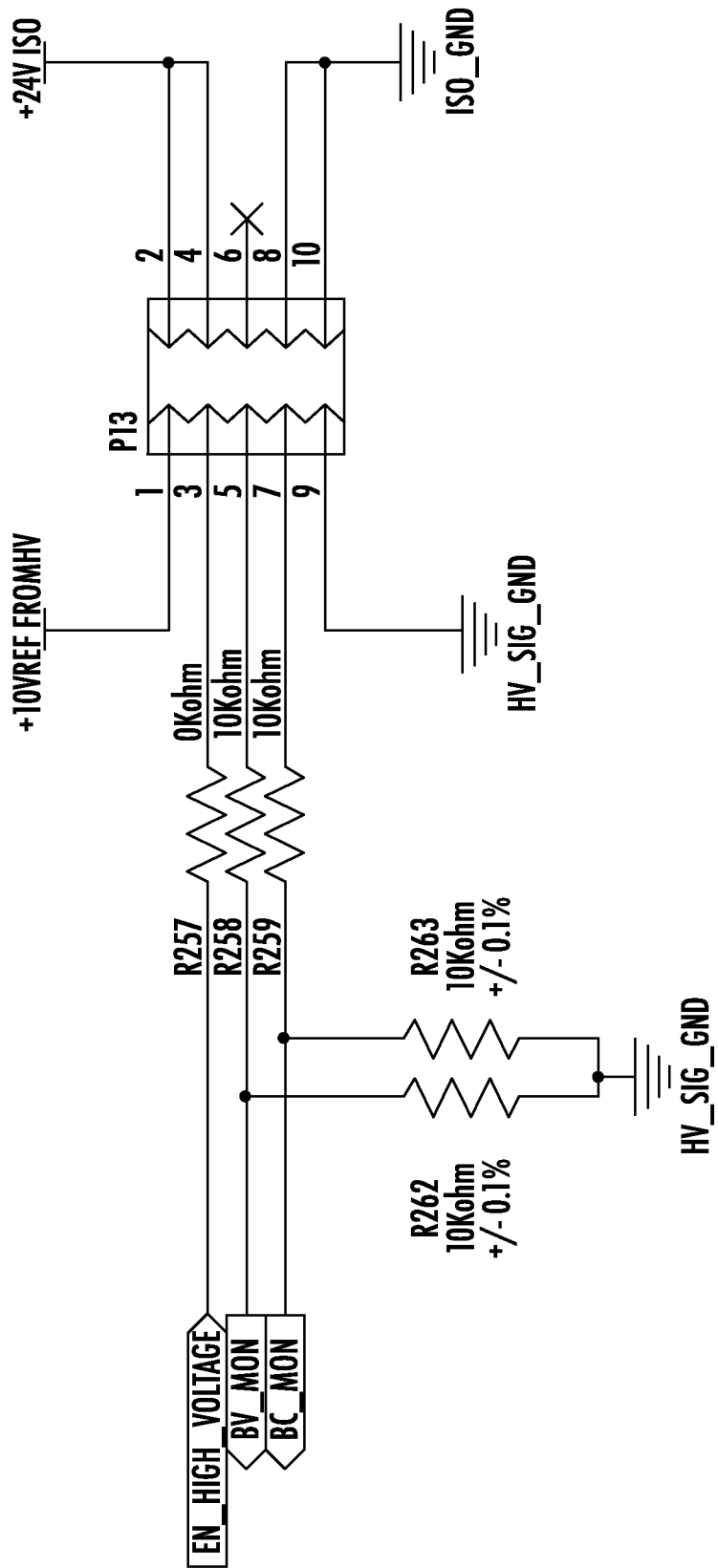

As shown in FIG. 5H, circuitry 570 comprises digital pot HV control circuitry. In some embodiments, digital pot HV control circuitry 294 may be implemented, in part or in whole, as circuitry 570. In some embodiments, the ADDR1 and ADDR0 pins of component U37 are connected to +3V3, which sets the I2C address to 0100000. In some embodiments, Rwb=(D/256)*Rab+55; 1108=(D/256)*10000+55; D=27; HEX Number for the program=0x001B. In one illustrative example embodiment, for a 400V applicator, the trip voltage is 1.33V (see capacity monitor, circuitry 530); VAR_CAP_V=1.33V; 1.33V=(12*Rwb)/(10,000 KOhm); Rwb=1108 Ohms; and Raw=10,000−1108=8892 Ohms.

As shown in FIG. 5I, circuitry 580 comprises HV supply monitor circuitry. In some embodiments, HV supply monitor circuitry 252 may be implemented, in part or in whole, as circuitry 580.

Figure 5J:
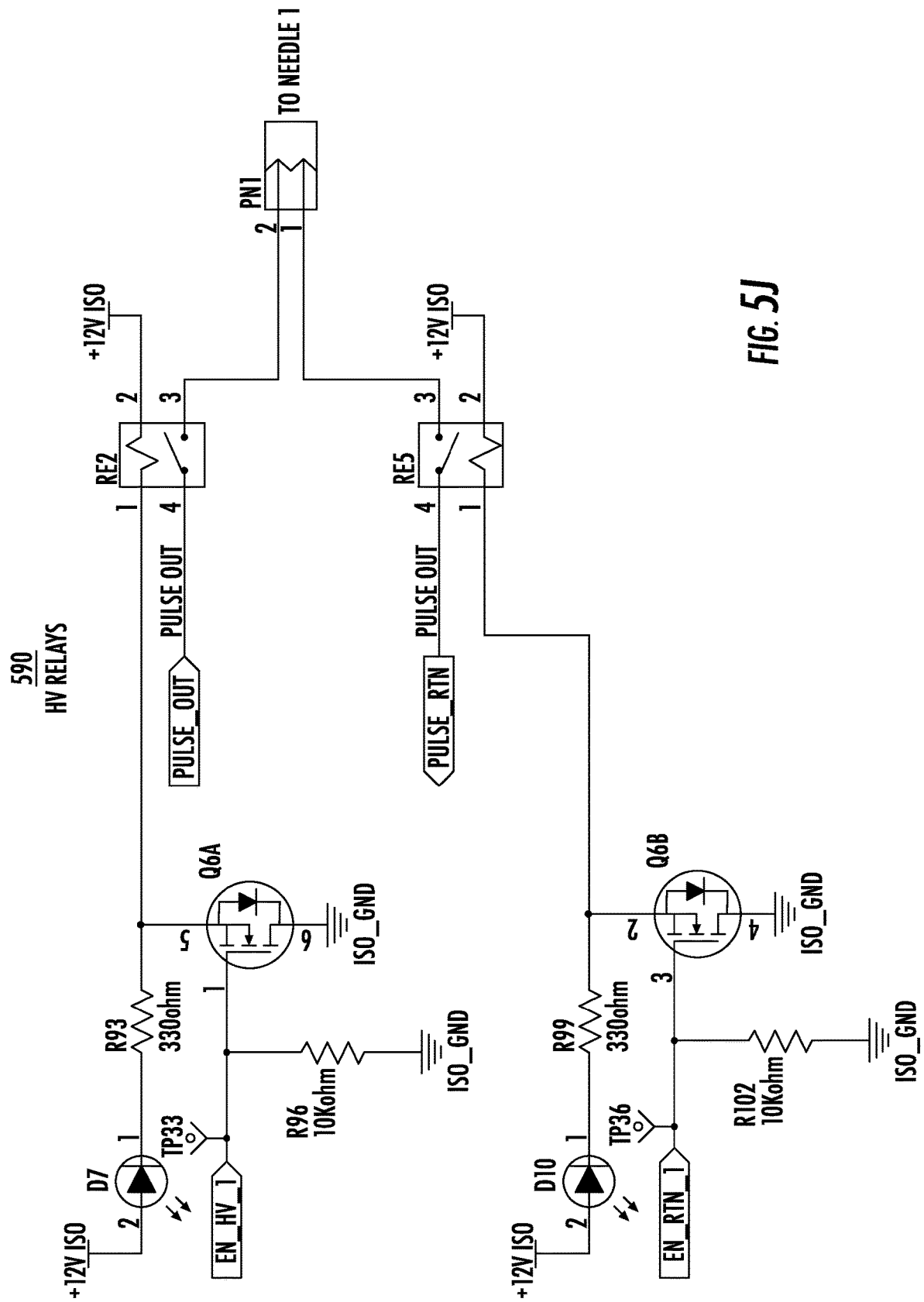

As shown in FIG. 5J, circuitry 590 comprises HV relay circuitry. In some embodiments, HV relay circuitry 222 may be implemented, in part or in whole, as circuitry 590. For example, where EPE circuitry 220 includes six EPE needle electrodes, HV relay circuitry 222 may include a circuitry 590 for each of the six EPE needle electrodes.

Figure 6A:
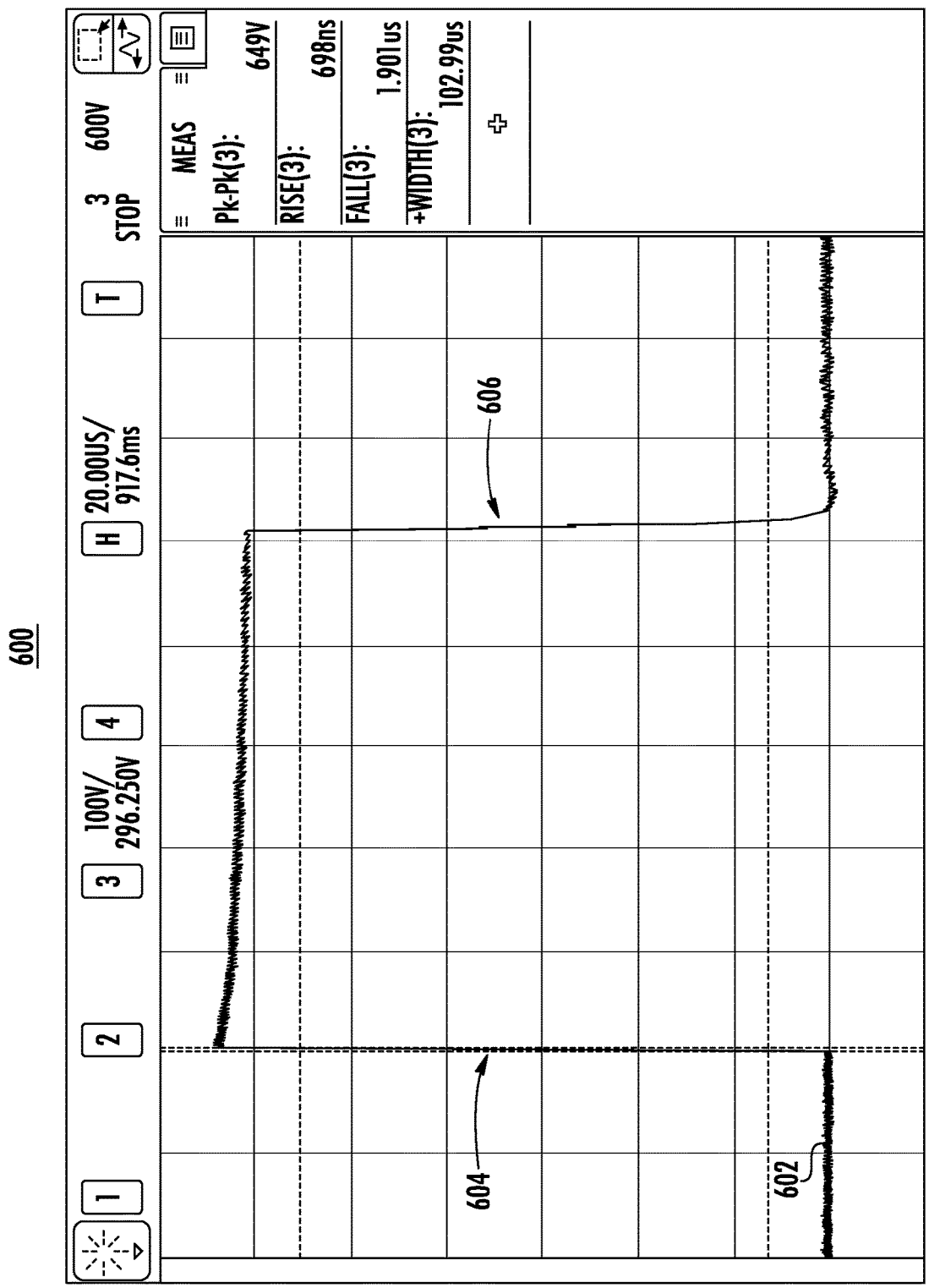
FIG. 6A, FIG. 6B, and FIG. 6C illustrate example pulse voltage signals in accordance with some example embodiments described herein.
Figure 6B:
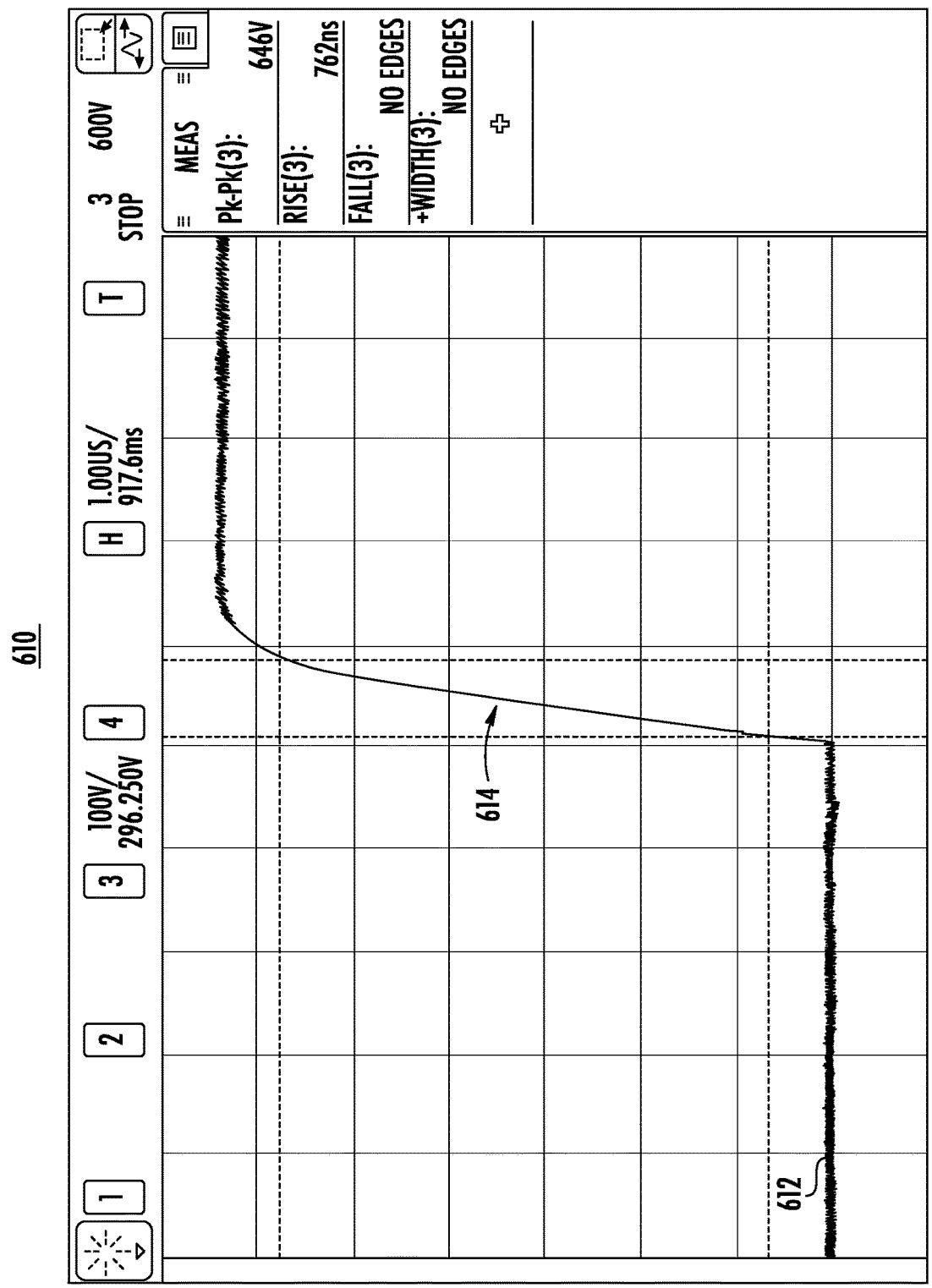
Figure 6C:
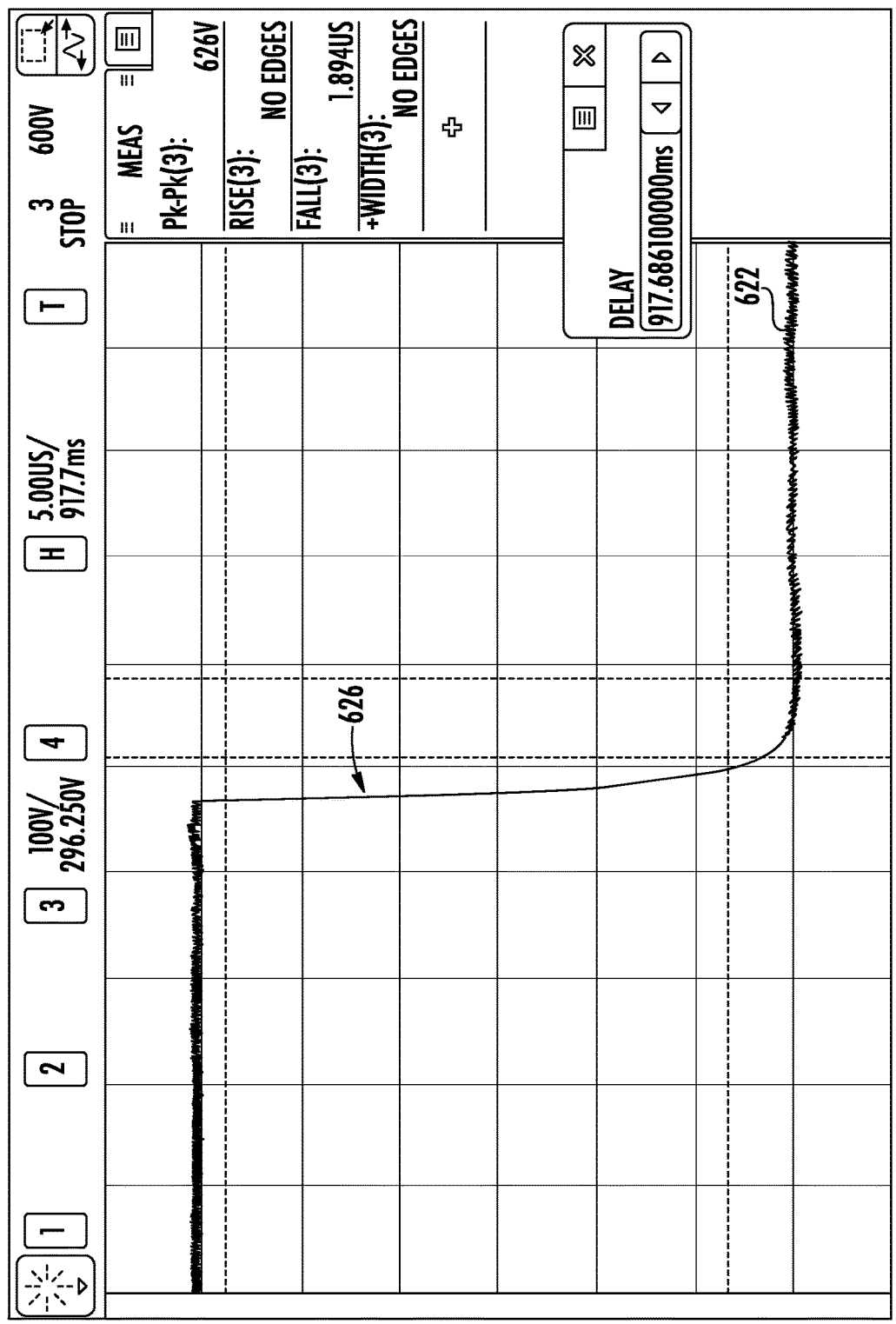

FIG. 6A, FIG. 6B, and FIG. 6C illustrate example pulse voltage signals in accordance with some example embodiments described herein. As shown in FIG. 6A, user interface display screen 600 shows an example pulse voltage signal 602 comprising a rising edge 604 and a falling edge 606 of a pulse in a set of pulses. In some embodiments, the pulse monitor analysis circuitry 276 may determine that: the width (e.g., duration) of the pulse in the set of pulses is 102.99 microseconds; the rise time of the rising edge 604 of the pulse in the set of pulses is 698 nanoseconds; the fall time of the falling edge 626 of the pulse in the set of pulses is 1.901 microseconds.

As shown in FIG. 6B, user interface display screen 610 shows an example pulse voltage signal 612 comprising a rising edge 614 of a pulse in a set of pulses. In some embodiments, the pulse monitor analysis circuitry 276 may determine that the rise time of the rising edge 614 of the pulse in the set of pulses is 762 nanoseconds.

As shown in FIG. 6B, user interface display screen 620 shows an example pulse voltage signal 622 comprising a falling edge 626 of a pulse in a set of pulses. In some embodiments, the pulse monitor analysis circuitry 276 may determine that the fall time of the falling edge 626 of the pulse in the set of pulses is 1.894 microseconds.

Having described specific components of example devices involved in the present disclosure, example procedures for providing an EPT treatment instrument configured to detect fault conditions are described below in connection with FIG. 7.

Figure 7:
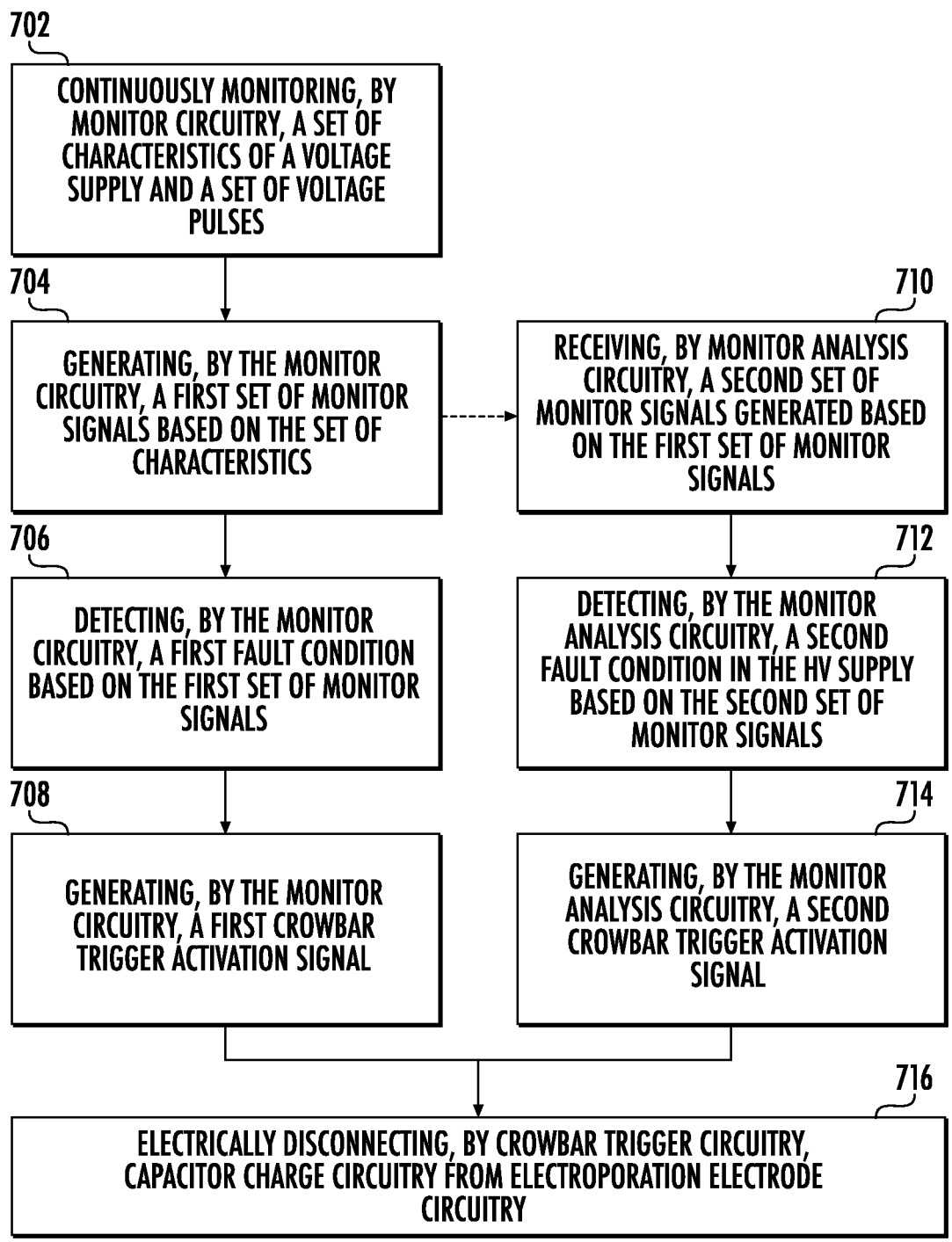
FIG. 7 illustrates an example flowchart illustrating an example method in accordance with some example embodiments described herein.

FIG. 7 illustrates an example flowchart 700 that contains example operations for detecting fault conditions while electroporating cells in a tissue using a set of voltage pulses generated based on a voltage supply according to some example embodiments described herein. The operations described in connection with FIG. 7 may, for example, be performed by one or more components described with reference to EPT treatment instrument 100 shown in FIG. 1; by apparatus 200 shown in FIG. 2; by any other component described herein; or by any combination thereof.

As shown by block 702, the apparatus 200 includes means, such as monitor circuitry 240 or the like, for continuously monitoring a set of characteristics of the voltage supply and the set of voltage pulses. In some embodiments, the set of characteristics may comprise HV voltage, capacitor voltage, pulse voltage, current, impedance voltage, HV supply voltage, HV supply current, any other suitable characteristics, or any combination thereof.

As shown by block 704, the apparatus 200 includes means, such as the monitor circuitry 240 or the like, for generating a first set of monitor signals based on the set of characteristics. In some embodiments, the first set of monitor signals may include a set of analog monitor signals, such as an analog continuously monitored HV voltage signal, an analog continuously monitored capacitor voltage signal, an analog continuously monitored pulse voltage signal, an analog continuously monitored current signal, an analog continuously monitored impedance voltage signal, an analog continuously monitored HV supply voltage signal, an analog continuously monitored HV supply current signal, any other suitable analog monitor signal, or any combination thereof. In some embodiments, the monitor circuitry may be configured to transmit the first set of monitor signals to any other circuitry described herein, such as to ADC circuitry (e.g., ADC circuitry 296). The ADC circuitry may provide for improved signal monitoring via faster sampling ADCs (e.g., 2,000,000 samples per second).

As shown by block 706, the apparatus 200 includes means, such as the monitor circuitry 240 or the like, for detecting a first fault condition based on the first set of monitor signals. The first fault condition may comprise an analog fault condition, such as an analog HV overvoltage condition, an analog capacitor overvoltage condition, an analog pulse overvoltage signal condition, an analog overcurrent signal condition, any other suitable analog fault condition, or any combination thereof.

As shown by block 708, the apparatus 200 includes means, such as the monitor circuitry 240 or the like, for generating a first crowbar trigger activation signal. In some embodiments, the monitor circuitry 240 may be configured to generate the first crowbar trigger activation signal in response to detecting the first fault condition. In some embodiments, the first crowbar trigger activation signal may comprise an analog crowbar trigger activation signal, such as an HV overvoltage signal (nHV_OV), a capacitor overvoltage signal (nCAP_OV), a pulse overvoltage signal (nPULSE_OV), an overcurrent signal (nOVER_CURRENT), any other suitable analog crowbar trigger activation signal, or any combination thereof. In some embodiments, the monitor circuitry 240 may be configured to transmit the first crowbar trigger activation signal to crowbar trigger circuitry (e.g., crowbar trigger circuitry 230).

As shown by block 710, the apparatus 200 includes means, such as monitor analysis circuitry 270 or the like, for receiving a second set of monitor signals generated based on the first set of monitor signals. The second set of monitor signals may include a set of digital monitor signals, such as a digital continuously monitored HV voltage signal, a digital continuously monitored capacitor voltage signal, a digital continuously monitored pulse voltage signal, a digital continuously monitored current signal, a digital continuously monitored impedance voltage signal, a digital continuously monitored HV supply voltage signal, a digital continuously monitored HV supply current signal, any other suitable digital monitor signal, or any combination thereof. In some embodiments, the monitor analysis circuitry 270 may be configured to receive the second set of monitor signals from to any other circuitry described herein, such as from ADC circuitry (e.g., ADC circuitry 296). For example, the first set of monitor signals may be a set of analog monitor signals transmitted by the monitor circuitry 240 to the ADC circuitry 296, and the second set of monitor signals may be a set of digital monitor signals generated by the ADC circuitry 296 based on the set of analog monitor signals and transmitted by the ADC circuitry 296 to the monitor analysis circuitry 270.

As shown by block 712, the apparatus 200 includes means, such as the monitor analysis circuitry 270 or the like, for detecting a second fault condition based on the second set of monitor signals. The second fault condition may comprise a digital fault condition, such as a digital HV overvoltage condition, a digital capacitor overvoltage condition, a digital pulse overvoltage signal condition, a digital overcurrent signal condition, any other suitable digital fault condition, or any combination thereof.

As shown by block 714, the apparatus 200 includes means, such as the monitor analysis circuitry 270 or the like, for generating a second crowbar trigger activation signal. In some embodiments, the monitor analysis circuitry 270 may be configured to generate the second crowbar trigger activation signal in response to detecting the second fault condition. In some embodiments, the second crowbar trigger activation signal may comprise a digital crowbar trigger activation signal (nMICRO_CROWBAR). In some embodiments, the monitor circuitry 240 may be configured to transmit the second crowbar trigger activation signal to crowbar trigger circuitry (e.g., crowbar trigger circuitry 230).

As shown by block 716, the apparatus 200 includes means, such as the monitor analysis circuitry 270 or the like, for: receiving either the first crowbar trigger activation signal or the second crowbar trigger activation signal; and, in response to either receiving the first crowbar trigger activation signal or receiving the second crowbar trigger activation signal, electrically disconnecting the capacitor charge circuitry from the electroporation electrode circuitry.

In some embodiments, operations 702, 704, 706, 708, 710, 712, 714, and 716 may not necessarily occur in the order depicted in FIG. 7. In some embodiments, one or more of the operations depicted in FIG. 7 may occur substantially simultaneously. In some embodiments, one or more additional operations may be involved before, after, or between any of the operations shown in FIG. 7.

As described above and with reference to FIG. 1, FIG. 2, FIG. 3A, FIG. 3B, FIG. 3C, FIG. 3D, FIG. 4A, FIG. 4B, FIG. 4C, FIG. 5A, FIG. 5B, FIG. 5C, FIG. 5D, FIG. 5E, FIG. 5F, FIG. 5G, FIG. 5H, FIG. 5I, FIG. 5J, FIG. 6A, FIG. 6B, FIG. 6C and FIG. 7, example embodiments of the present disclosure thus provide an EPT treatment instrument that provides for: electroporating cells in a tissue using a set of voltage pulses generated based on a voltage supply; continuously monitoring a set of characteristics of the voltage supply and the set of voltage pulses; generating a set of analog monitor signals based on the set of characteristics; detecting a first fault condition (e.g., overvoltage, overcurrent) based on the analog set of monitor signals; detecting a second fault condition (e.g., overvoltage, overcurrent) based on a set of digital monitor signals; and in response to either the detection of the first fault condition or the second fault condition, electrically disconnecting, by crowbar trigger circuitry, the voltage pulses and the voltage supply from the electroporation electrode needles to prevent the overvoltages and overcurrents from being applied to the patient. Accordingly, the example embodiments of the present disclosure provide: improved detection of a fault condition (e.g., overvoltage, overcurrent) by multiple, redundant analog and digital circuitries; and improved prevention, by crowbar trigger circuitry, of any overvoltages or overcurrents from being applied to a patient.

FIG. 7 thus illustrates an example flowchart describing operations performed in accordance with example embodiments of the present disclosure. It will be understood that each block of the flowchart, and combinations of blocks in the flowchart, may be implemented by various means, such as devices comprising hardware, firmware, one or more processors, and/or circuitry associated with execution of software comprising one or more computer program instructions. For example, one or more of the procedures described above may be performed by execution of program code instructions. In this regard, the program code instructions that, when executed, cause performance of the procedures described above may be stored by a non-transitory computer-readable storage medium (e.g., memory 264) of a computing apparatus (e.g., apparatus 200) and executed by a processor (e.g., processor 262) of the computing apparatus. In this regard, the computer program instructions which embody the procedures described above may be stored by a memory of an apparatus employing an embodiment of the present disclosure and executed by a processor of the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowchart 700. When executed, the instructions stored in the computer-readable storage memory produce an article of manufacture configured to implement the various functions specified in the flowchart 700. The program code instructions may also be loaded onto a computer or other programmable apparatus to cause a series of operations to be performed on the computer or other programmable apparatus to produce a computer-implemented process such that the instructions executed on the computer or other programmable apparatus provide operations for implementing the functions specified in the operations of flowchart 700. Moreover, execution of a computer or other processing circuitry to perform various functions converts the computer or other processing circuitry into a particular machine configured to perform an example embodiment of the present disclosure.

The flowchart operations described with reference to FIG. 7 support combinations of means for performing the specified functions and combinations of operations for performing the specified functions. It will be understood that one or more operations of the flowchart, and combinations of operations in the flowchart, may be implemented by special purpose hardware-based computer systems which perform the specified functions, or combinations of special purpose hardware and computer instructions.

In some example embodiments, certain ones of the operations herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," and similar words are not intended to limit the order of the steps; these words are simply used to guide the reader through the description of the methods. Further, any reference to claim elements in the singular, for example, using the articles "a," "an" or "the," is not to be construed as limiting the element to the singular and may, in some instances, be construed in the plural.

While various embodiments in accordance with the principles disclosed herein have been shown and described above, modifications thereof may be made by one skilled in the art without departing from the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present disclosure. Furthermore, any advantages and features described above may relate to specific embodiments, but shall not limit the application of such issued claims to processes and structures accomplishing any or all of the above advantages or having any or all of the above features.

In addition, the section headings used herein are provided for consistency with the suggestions under 37 C.F.R. § 1.77 or to otherwise provide organizational cues. These headings shall not limit or characterize the disclosure set out in any claims that may issue from this disclosure. For instance, a description of a technology in the "Background" is not to be construed as an admission that certain technology is prior art to any disclosure in this disclosure. Neither is the "Summary" to be considered as a limiting characterization of the disclosure set forth in issued claims. Furthermore, any reference in this disclosure to "disclosure" or "embodiment" in the singular should not be used to argue that there is only a single point of novelty in this disclosure. Multiple embodiments of the present disclosure may be set forth according to the limitations of the multiple claims issuing from this disclosure, and such claims accordingly define the disclosure, and their equivalents, that are protected thereby. In all instances, the scope of the claims shall be considered on their own merits in light of this disclosure, but should not be constrained by the headings set forth herein.

Also, techniques, systems, subsystems, and methods described and illustrated in the various embodiments as discrete or separate may be combined or integrated with other systems, modules, techniques, or methods without departing from the scope of the present disclosure. Other devices or components shown or discussed as coupled to, or in communication with, each other may be indirectly coupled through some intermediate device or component, whether electrically, mechanically, or otherwise. Other examples of changes, substitutions, and alterations are ascertainable by one skilled in the art and could be made without departing from the scope disclosed herein.

Many modifications and other embodiments of the disclosure set forth herein will come to mind to one skilled in the art to which these embodiments pertain having the benefit of teachings presented in the foregoing descriptions and the associated figures. Although the figures only show certain components of the apparatus and systems described herein, it is understood that various other components may be used in conjunction with the components and structures disclosed herein. Therefore, it is to be understood that the disclosure is not to be limited to the specific embodiments disclosed and that modifications and other embodiments are intended to be included within the scope of the appended claims. For example, the various elements or components may be combined, rearranged, or integrated in another system or certain features may be omitted or not implemented. Moreover, the steps in any method described above may not necessarily occur in the order depicted in the accompanying drawings, and in some cases one or more of the steps depicted may occur substantially simultaneously, or additional steps may be involved. Although specific terms are employed herein, they are used in a generic and descriptive sense only and not for purposes of limitation.

The invention claimed is:

1. A system for electroporating cells in a tissue using a set of voltage pulses generated based on a voltage supply, the system comprising:
a first monitor circuitry, wherein the first monitor circuitry is in electrical communication with at least one of a voltage generation circuitry that is coupled to a capacitor charge circuitry or an electroporation electrode (EPE) circuitry, and wherein the first monitor circuitry is configured to:
receive a first set of monitor signals,
detect a first fault condition based on the first set of monitor signals,
in response to a detection of the first fault condition, transmit first instructions configured to cause termination of electroporation; and
a second monitor circuitry, wherein the second monitor circuitry is in electrical communication with at least one of the voltage generation circuitry or the EPE circuitry, and wherein the second monitor circuitry is configured to:
receive a second set of monitor signals,
detect a second fault condition based on the second set of monitor signals,
in response to a detection of the second fault condition, transmit second instructions configured to cause termination of electroporation,
wherein the second set of monitor signals is based on the first set of monitor signals, wherein the first set of monitor signals is a set of analog monitor signals, wherein the second set of monitor signals is a set of digital monitor signals.

2. The system of claim 1, wherein the first monitor circuitry comprises an impedance monitor circuitry, wherein the impedance monitor circuitry is configured to:
monitor a resistance of the tissue,
generate a first monitored impedance voltage signal based on the monitored resistance, and
detect a first impedance testing fault condition based on the first monitored impedance voltage signal.

3. The system of claim 2, wherein the first monitor circuitry is in electrical communication with the electroporation electrode (EPE) circuitry and wherein the impedance monitor circuitry is configured to:
generate a set of low voltage (LV) pulses,
transmit the set of LV pulses to the EPE circuitry,
receive a set of LV return pulses from the EPE circuitry, and
monitor the resistance of the tissue based on the set of LV return pulses.

4. The system of claim 1, wherein the first monitor circuitry is in electrical communication with the electroporation electrode (EPE) circuitry and wherein the EPE circuitry comprises a relay circuitry in electronic communication with an EPE needle circuitry, wherein the relay circuitry comprises a first relay and a second relay, wherein the first monitor circuitry is configured to:
in response to the detection of the first fault condition, generate a first set of deactivation signals, and
transmit the first set of deactivation signals to the EPE circuitry, wherein the second monitor circuitry is configured to:
in response to the detection of the second fault condition, generate a second set of deactivation signals, and
transmit the second set of deactivation signals to the EPE circuitry.

5. The system of claim 4, wherein each of the first relay and the second relay is configured to:
receive one of deactivation signals in the first set of deactivation signals or in the second set of deactivation signals, and
in response to receipt of the one of the deactivation signals, electrically disconnect the capacitor charge circuitry from the EPE circuitry.

6. The system of claim 1, wherein the voltage supply is a HV supply, and wherein a voltage of the HV supply is between about 1,000 volts and 1,750 volts.

7. The system of claim 6, wherein the voltage of the HV supply is about 1,500 volts.

8. The system of claim 1, wherein a duration of each voltage pulse in the set of voltage pulses is between about 50 microseconds and about 150 microseconds.

9. The system of claim 1, wherein the capacitor charge circuitry is in electrical communication with the voltage generation circuitry, a crowbar trigger circuitry, the first monitor circuitry, and the EPE circuitry, and wherein the capacitor charge circuitry is configured to:
receive the voltage supply from the voltage generation circuitry,
generate the set of voltage pulses based on the voltage supply, and
transmit the set of voltage pulses to the EPE circuitry.

10. The system of claim 9, wherein the first monitor circuitry is in electrical communication with the electroporation electrode (EPE) circuitry and wherein the first monitor circuitry is configured to:
continuously monitor a set of characteristics of the voltage supply and the set of voltage pulses,
generate the first set of monitor signals based on the set of characteristics, transmit the first set of monitor signals,
detect the first fault condition based on the first set of monitor signals,
in response to the detection of the first fault condition, generate a first crowbar trigger activation signal, and
transmit the first crowbar trigger activation signal to the crowbar trigger circuitry;
wherein the second monitor circuitry is configured to:
in response to the detection of the second fault condition, generate a second crowbar trigger activation signal, and
transmit the second crowbar trigger activation signal to the crowbar trigger circuitry.

11. The system of claim 10, wherein the crowbar trigger circuitry is in electrical communication with the first monitor circuitry and the second monitor circuitry, and wherein the crowbar trigger circuitry is configured to:
receive the first crowbar trigger activation signal from the first monitor circuitry,
receive the second crowbar trigger activation signal from the second monitor circuitry, and
in response to either a receipt of the first crowbar trigger activation signal or a receipt of the second crowbar trigger activation signal, electrically disconnect the capacitor charge circuitry from the EPE circuitry.

12. The system of claim 11, wherein the crowbar trigger circuitry is configured to electrically disconnect the capacitor charge circuitry from the EPE circuitry within about 10 microseconds of the detection of the first fault condition or the detection of the second fault condition.

13. The system of claim 12, wherein the voltage supply is a high voltage (HV) supply, and wherein the first monitor circuitry comprises a first HV monitor circuitry configured to:
continuously monitor an HV voltage of an HV supply, wherein the set of characteristics comprises the continuously monitored HV voltage,
generate a first continuously monitored HV voltage signal based on the continuously monitored HV voltage, wherein the first set of monitor signals comprises the first continuously monitored HV voltage signal,
detect a first HV overvoltage condition based on the first continuously monitored HV voltage signal, wherein the first fault condition is the first HV overvoltage condition, and
in response to a detection of the first HV overvoltage condition, generate a first HV overvoltage signal, wherein the first crowbar trigger activation signal is the first HV overvoltage signal.

14. The system of claim 13, wherein the second monitor circuitry comprises a second HV monitor circuitry and a crowbar trigger control signal generation circuitry, wherein the second HV monitor circuitry is configured to:
receive a second continuously monitored HV voltage signal based on the first continuously monitored HV voltage signal, wherein the second set of monitor signals comprises the second continuously monitored HV voltage signal,
detect a second HV overvoltage condition based on the second continuously monitored HV voltage signal, wherein the second fault condition is the second HV overvoltage condition,
in response to a detection of the second HV overvoltage condition, generate a second HV overvoltage signal, and
transmit the second HV overvoltage signal to the crowbar trigger control signal generation circuitry; and
wherein the crowbar trigger control signal generation circuitry is configured to:
receive the second HV overvoltage signal from the second HV monitor circuitry,
in response to receipt of the second HV overvoltage signal, generate the second crowbar trigger activation signal, and
transmit the second crowbar trigger activation signal to the crowbar trigger circuitry.

15. The system of claim 10, wherein the first monitor circuitry comprises a first capacity monitor circuitry configured to:
continuously monitor a capacitor voltage of the capacitor charge circuitry, wherein the set of characteristics comprises the continuously monitored capacitor voltage,
generate a first continuously monitored capacitor voltage signal based on the continuously monitored capacitor voltage, wherein the first set of monitor signals comprises the first continuously monitored capacitor voltage signal,
detect a first capacitor overvoltage condition based on the first continuously monitored capacitor voltage signal, wherein the first fault condition is the first capacitor overvoltage condition, and
in response to a detection of the first capacitor overvoltage condition, generate a first capacitor overvoltage signal, wherein the first crowbar trigger activation signal is the first capacitor overvoltage signal.

16. The system of claim 15, wherein the second monitor circuitry comprises a second capacity monitor circuitry and a crowbar trigger control signal generation circuitry,
wherein the second capacity monitor circuitry is configured to:
receive a second continuously monitored capacitor voltage signal based on the first continuously monitored capacitor voltage signal, wherein the second set of monitor signals comprises the second continuously monitored capacitor voltage signal,
detect a second capacitor overvoltage condition based on the second continuously monitored capacitor voltage signal, wherein the second fault condition is the second capacitor overvoltage condition,
in response to a detection of the second capacitor overvoltage condition, generate a second capacitor overvoltage signal, and
transmit the second capacitor overvoltage signal to the crowbar trigger control signal generation circuitry; and
wherein the crowbar trigger control signal generation circuitry is configured to:
receive the second capacitor overvoltage signal from the second capacity monitor circuitry, in response to receipt of the second capacitor overvoltage signal, generate the second crowbar trigger activation signal, and transmit the second crowbar trigger activation signal to the crowbar trigger circuitry.

17. The system of claim 10, wherein the first monitor circuitry comprises a first pulse monitor circuitry configured to:

continuously monitor a pulse voltage of the set of voltage pulses, wherein the set of characteristics comprises the continuously monitored pulse voltage, generate a first continuously monitored pulse voltage signal based on the continuously monitored pulse voltage, wherein the first set of monitor signals comprises the first continuously monitored pulse voltage signal, detect a first pulse overvoltage condition based on the first continuously monitored pulse voltage signal, wherein the first fault condition is the first pulse overvoltage condition, and in response to a detection of the first pulse overvoltage condition, generate a first pulse overvoltage signal, wherein the first crowbar trigger activation signal is the first pulse overvoltage signal.

18. A method for electroporating cells in a tissue using a set of voltage pulses generated based on a voltage supply, the method comprising:

generating, by a first monitor circuitry, a first set of monitor signals, wherein the first monitor circuitry is in electrical communication with an electroporation electrode (EPE) circuitry;

detecting, by the first monitor circuitry, a first fault condition based on the first set of monitor signals;

in response to a detection of the first fault condition, transmitting first instructions configured to cause termination of electroporation;

receiving, by a second monitor circuitry, a second set of monitor signals;

detecting, by the second monitor circuitry, a second fault condition based on the second set of monitor signals;

in response to a detection of the second fault condition, transmitting second instructions configured to cause termination of electroporation, wherein the second set of monitor signals is based on the first set of monitor signals, wherein the first set of monitor signals is a set of analog monitor signals, wherein the second set of monitor signals is a set of digital monitor signals.

* * * * *